US009770227B2

(12) United States Patent
Kawabata et al.

(10) Patent No.: US 9,770,227 B2
(45) Date of Patent: Sep. 26, 2017

(54) ULTRASOUND DIAGNOSTIC APPARATUS AND ULTRASOUND MEASUREMENT METHOD USING SAME

(75) Inventors: Akihiro Kawabata, Kanagawa (JP); Manabu Migita, Kanagawa (JP); Takenori Fukumoto, Kanagawa (JP); Makiko Urabe, Kanagawa (JP)

(73) Assignee: KONICA MINOLTA, INC., Tokyo (JP)

(*) Notice: Subject to any disclaimer, the term of this patent is extended or adjusted under 35 U.S.C. 154(b) by 968 days.

(21) Appl. No.: 14/000,702

(22) PCT Filed: Jun. 7, 2012

(86) PCT No.: PCT/JP2012/003723
§ 371 (c)(1),
(2), (4) Date: Aug. 21, 2013

(87) PCT Pub. No.: WO2012/172756
PCT Pub. Date: Dec. 20, 2012

(65) Prior Publication Data
US 2013/0331700 A1 Dec. 12, 2013

(30) Foreign Application Priority Data

Jun. 13, 2011 (JP) ................................ 2011-130873

(51) Int. Cl.
A61B 8/08 (2006.01)
A61B 8/00 (2006.01)
A61B 8/14 (2006.01)

(52) U.S. Cl.
CPC .......... *A61B 8/5246* (2013.01); *A61B 8/0858* (2013.01); *A61B 8/0883* (2013.01);
(Continued)

(58) Field of Classification Search
CPC .... A61B 5/02007; A61B 8/4281; A61B 8/463
See application file for complete search history.

(56) References Cited

U.S. PATENT DOCUMENTS

| 2004/0116812 A1 | 6/2004 | Selzer et al. |
| 2005/0267365 A1 | 12/2005 | Sokulin |
| 2008/0171939 A1 | 7/2008 | Ishihara |
| 2009/0227867 A1 | 9/2009 | Suzuki et al. |

FOREIGN PATENT DOCUMENTS

| EP | 1-958-571 | 8/2008 |
| JP | 2005-000390 A | 1/2005 |

(Continued)

OTHER PUBLICATIONS

Extended European Search Report, dated Oct. 14, 2014, Application No. 12800539.4 (8 pages).

(Continued)

*Primary Examiner* — Joseph M Santos Rodriguez
(74) *Attorney, Agent, or Firm* — Lucas & Mercanti, LLP

(57) ABSTRACT

An ultrasonic diagnostic apparatus according to the present disclosure is configured so that a probe including transducers is connectable thereto and performs predetermined measuring processing on a subject's region of interest. The apparatus includes a controller, which performs transmission processing, in which an ultrasonic wave is transmitted toward the subject including the region of interest by driving the probe, and received signal processing, in which frames are generated based on the probe's received signals representing the ultrasonic wave reflected from the subject including the region of interest, a number of times at mutually different times, thereby generating multiple frames, which selects at least two frames under measurement to be subjected to measurement from the multiple frames, which extracts measurable ranges, where the measuring processing can be carried out, based on respective received signals obtained from the region of interest represented in the at least two frames under measurement, and which combines those measurable ranges together to perform predetermined measuring processing on the region of interest.

15 Claims, 14 Drawing Sheets

(52) U.S. Cl.
CPC .............. *A61B 8/0891* (2013.01); *A61B 8/14* (2013.01); *A61B 8/483* (2013.01); *A61B 8/5223* (2013.01); *A61B 8/5284* (2013.01); *A61B 8/54* (2013.01); *A61B 8/543* (2013.01)

(56) References Cited

FOREIGN PATENT DOCUMENTS

| JP | 2007-159920 A | 6/2007 |
|---|---|---|
| JP | 2008-168016 A | 7/2008 |
| JP | 2010-022565 A | 2/2010 |

OTHER PUBLICATIONS

International Search Report for corresponding International Application No. PCT/JP2012/003723 mailed Aug. 7, 2012.

Stein et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force Endorsed by the Society for Vascular Medicine", Journal of the American Society of Echocardiography, Feb. 2008 (pp. 93 to 111).

FIG.3
(a)
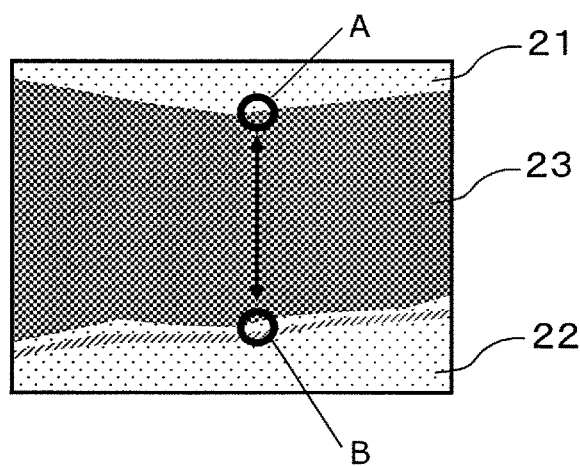
(b)
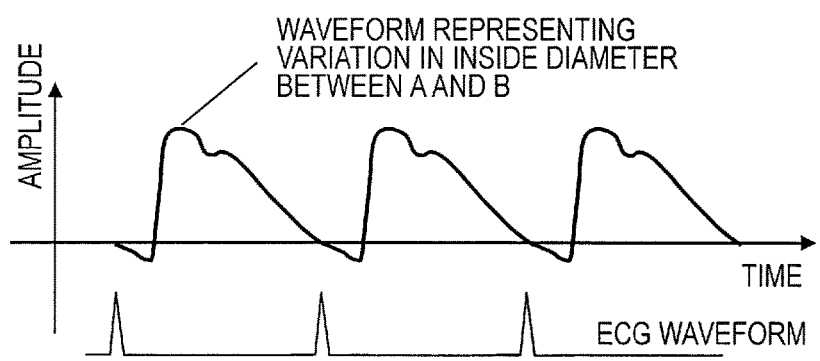

FIG.4
(a)
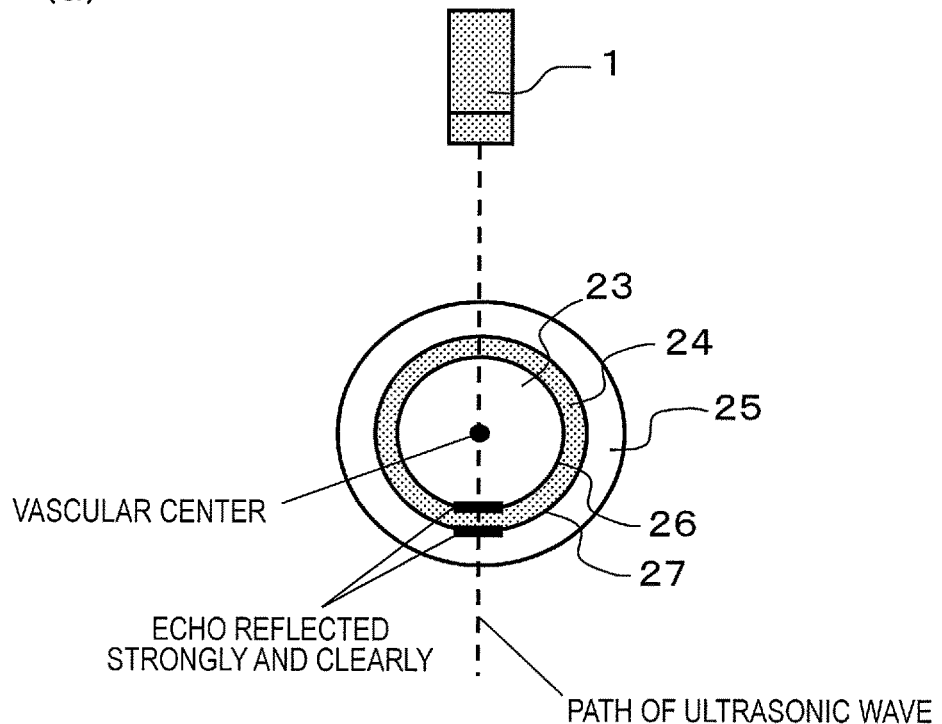
(b)
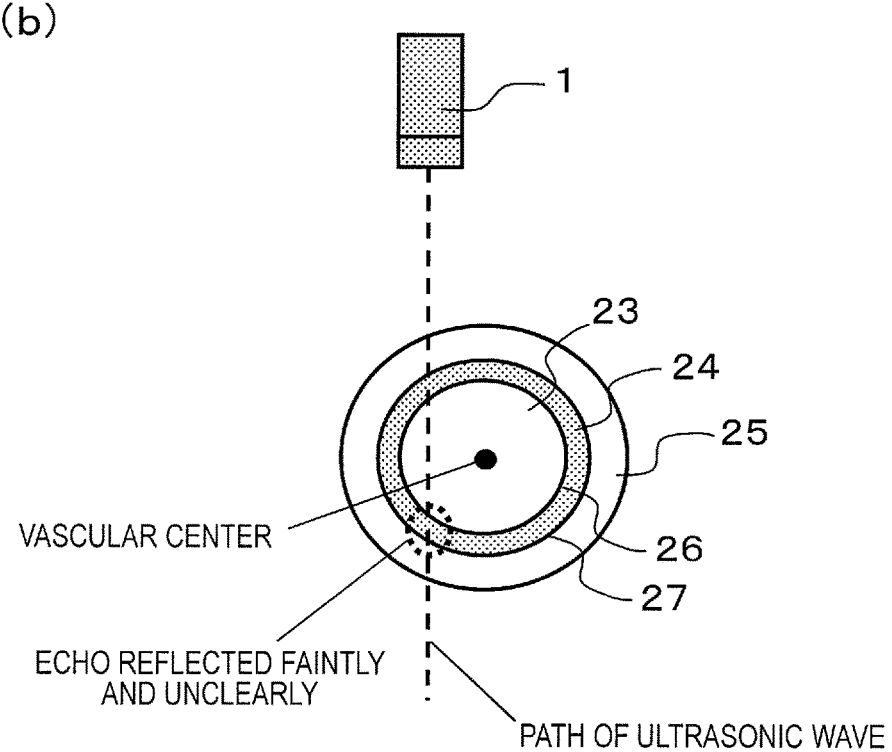

FIG.6
(a)
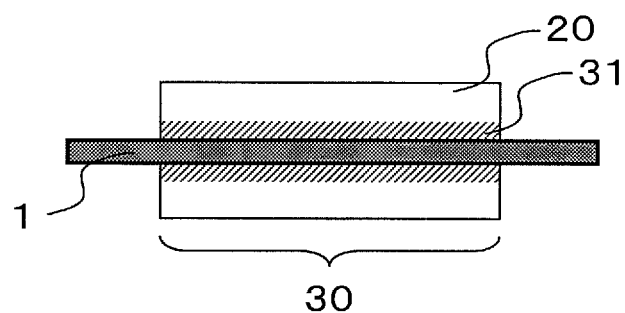
(b)
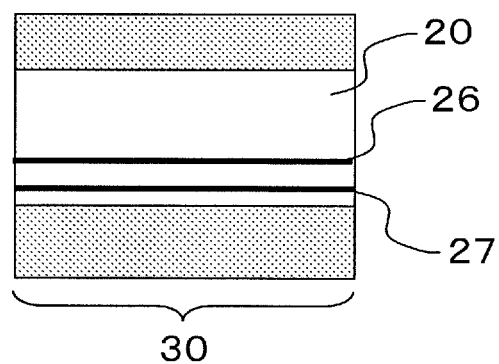

FIG. 7
(a)
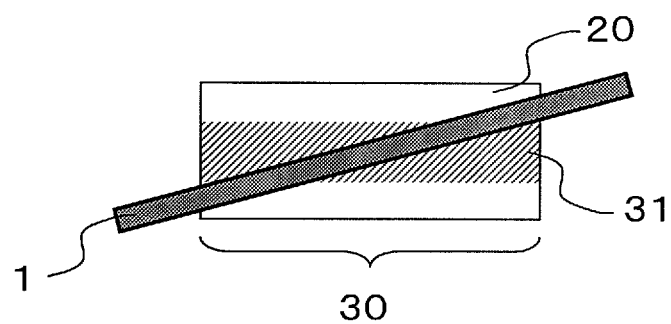
(b)
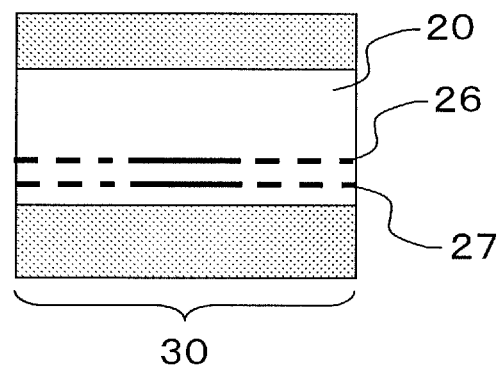

FIG.8
(a)
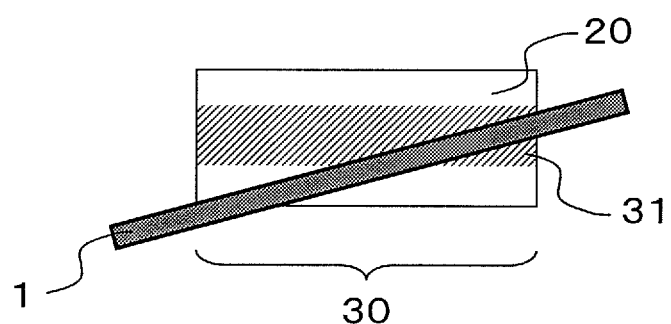
(b)
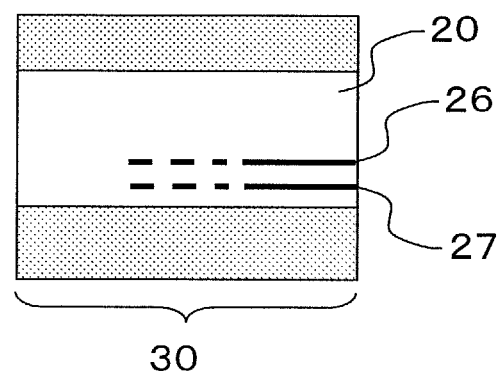

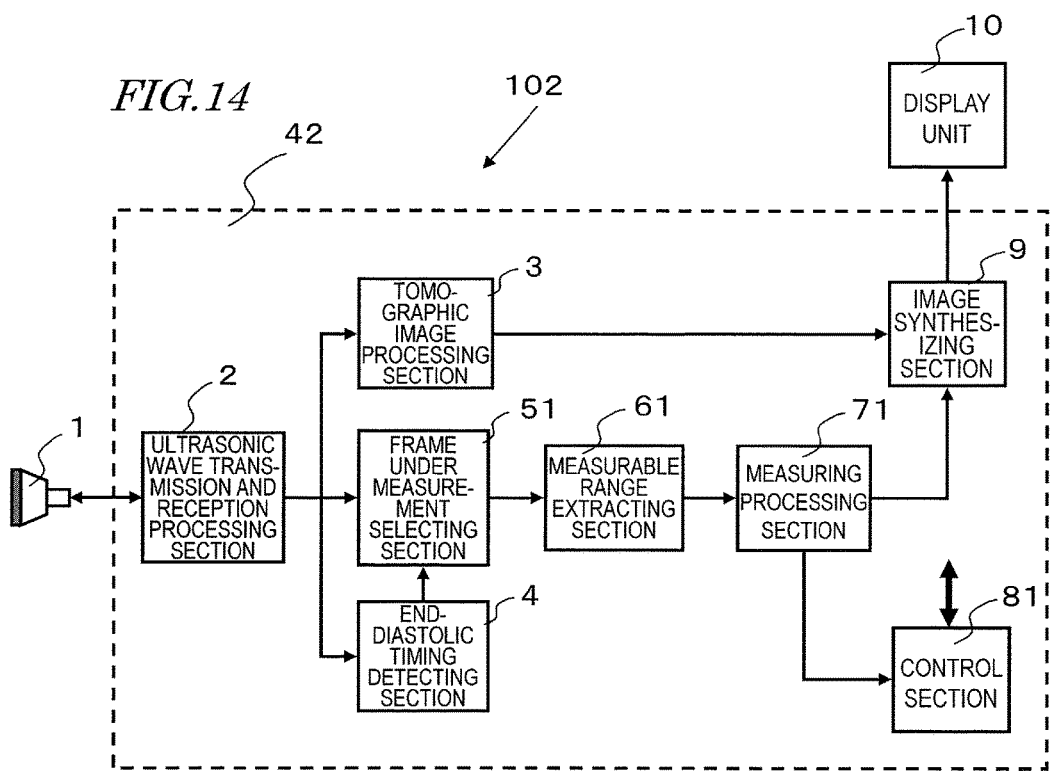
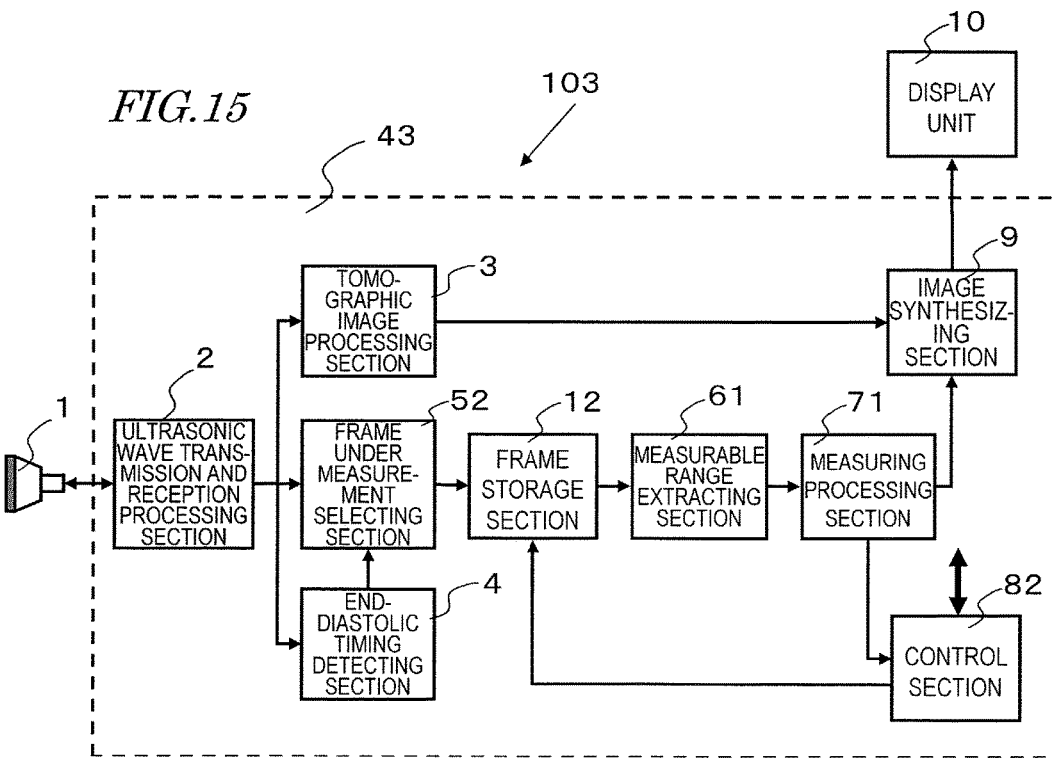

ULTRASOUND DIAGNOSTIC APPARATUS AND ULTRASOUND MEASUREMENT METHOD USING SAME

TECHNICAL FIELD

The present application relates to an ultrasonic diagnostic apparatus and an ultrasonic measuring method using the apparatus.

BACKGROUND ART

In making a diagnosis of arterial sclerosis, the intima-media thickness (which will be abbreviated herein as "IMT") of a carotid artery is known as one of most important indices to the status of an initial atherosclerotic. The "IMT" refers to the thickness of a complex of the intima and the media of a vascular wall of a carotid artery. In FIG. 16, the IMT refers to the thickness of a layer (i.e., an intima-media 24) that is seen between the lumen 23 and adventitia 25 of a blood vessel.

The IMT is generally obtained by detecting the boundary between the lumen 23 and intima of the blood vessel (which will be referred to herein as a "lumen-intima boundary 26") and the boundary between the media and the adventitia 25 (which will be referred to herein as a "media-adventitia boundary 27") and measuring the distance between these two boundaries using an ultrasonic diagnostic apparatus. For example, Patent Documents Nos. 1 and 2 disclose an ultrasonic diagnostic apparatus which measures the IMT automatically.

In measuring the IMT, ordinarily a predetermined IMT measuring range 30 is set in the long-axis direction of the carotid artery 20 (i.e., the direction in which the blood vessel extends) as shown in FIG. 16 and either the maximum thickness (max IMT) or average thickness (mean IMT) of the IMTs measured in the IMT measuring range 30 is regarded as an IMT value. For example, Non-Patent Document No. 1 recommends that the IMT measuring range 30 be set at 1 cm away from the far end (i.e., closer to the head) of the common carotid artery (CCA) of the carotid artery 20.

CITATION LIST

Patent Literature

Patent Document No. 1: Japanese Laid-Open Patent Publication No. 2008-168016
Patent Document No. 2: Japanese Laid-Open Patent Publication No. 2010-022565

Non-Patent Literature

Non-Patent Document No. 1: Journal of the American Society of Echocardiography, February 2008 (pp. 93 to 111)

SUMMARY OF INVENTION

Technical Problem

If the status of a blood vessel, which is the object of measuring, is going to be checked using a conventional ultrasonic diagnostic apparatus, however, nobody but a well experienced skilled person could make an accurate measurement, which is a problem with the prior art.

For example, in measuring the IMT, ultrasonic beams are transmitted and received with a probe put on the surface of a subject's neck so that the long-axis direction of his or her carotid artery is aligned with the longitudinal direction of the probe surface. At this time, the IMT can be measured accurately if the probe is arranged so that the vicinity of the center of a cross section that intersects with the long-axis direction of the carotid artery at right angles (such a cross section will be referred to herein as a "short-axis cross section") is scanned with the ultrasonic beam transmitted from the probe (i.e., so that the center axis of the carotid artery is scanned with the ultrasonic beam). In this description, a probe arranged at such a position will be referred to herein as a "probe catching the vicinity of the center of the short-axis cross section of the blood vessel".

However, just by checking the subject's skin surface, nobody can see where his or her carotid artery is and what shape the artery has. In addition, the carotid artery itself is very thin and its position or shape varies from one person to another. That is why it is not easy to put the probe at such a position where the probe can catch the vicinity of the center of a short-axis cross section of the carotid artery. For that reason, under the circumstances such as these, only a well-experienced skilled person can measure the IMT accurately and almost nobody can measure the IMT easily.

Meanwhile, even if some operator has managed to put the probe at such a position where the IMT can be measured accurately, he or she still needs to keep the probe fixed at such a position by holding the probe in hand. Consequently, it is not easy for the operator to measure the IMT accurately while keeping the probe fixed at such an appropriate position.

A non-limiting exemplary embodiment of the present application provides an ultrasonic diagnostic apparatus and measuring method using the apparatus, by which even a non-skilled person can measure the IMT accurately.

Solution to Problem

An ultrasonic diagnostic apparatus according to an aspect of the present invention is configured so that a probe including transducers is connectable to the apparatus and performs predetermined measuring processing on a subject's region of interest. The apparatus includes a controller. The controller performs transmission processing, in which an ultrasonic wave is transmitted toward the subject including the region of interest, by driving the probe, and received signal processing, in which frames are generated based on the probe's received signals representing the ultrasonic wave that has been reflected from the subject including the region of interest, a number of times at mutually different points in time, thereby generating multiple frames. The controller selects at least two frames under measurement to be subjected to measurement from the multiple frames. The controller extracts measurable ranges, on which the measuring processing is able to be carried out, based on respective received signals obtained from the region of interest that is represented in the at least two frames under measurement. And the controller combines those measurable ranges together to perform predetermined measuring processing on the region of interest.

An ultrasonic measuring method according to an aspect of the present invention is a method for carrying out a predetermined kind of measurement on a subject's region of interest using an ultrasonic wave generated by a probe. The method includes the steps of: (i) generating multiple frames by performing transmission processing, in which the ultrasonic wave is transmitted by driving the probe, and received signal processing, in which the frames are generated based on the probe's received signals representing the ultrasonic wave that has been reflected from the subject, including the region of interest, a number of times at mutually different points in time; (ii) selecting at least two frames under measurement to be subjected to measurement from those frames; (iii) extracting measurable ranges, on which the measuring processing is able to be carried out, based on respective received signals obtained from the region of interest that is represented in the at least two frames under measurement; and (iv) combining the tomographic image portions on the measurable ranges together to perform predetermined measuring processing on the region of interest.

Advantageous Effects of Invention

With the ultrasonic diagnostic apparatus disclosed in the present application, even if the probe that has been put on the subject has shifted from his or her region of interest, there is no need to adjust the position of the probe exactly to cancel the shift. Instead, by combining multiple frames under measurement together, measuring processing can be carried out appropriately.

That is to say, even if the probe is not put exactly at such an appropriate position where the state of the region of interest can be measured properly, measurement can still be done properly on the region of interest. As a result, even a non-skilled person can make an accurate measurement easily.

BRIEF DESCRIPTION OF DRAWINGS

FIG. 3(*a*) illustrates a cross section of a carotid artery in the long-axis direction, and FIG. 3(*b*) illustrates a waveform showing a variation in the inside diameter of the carotid artery with time as the heart pumps out blood.

FIGS. 4(*a*) and 4(*b*) illustrate the relative positions of a probe put on the subject with respect to a short-axis cross section of the blood vessel.

FIG. 6(*a*) is a top view illustrating an exemplary relative position of a probe with respect to the carotid artery during IMT measurement, and FIG. 6(*b*) illustrates a tomographic image representing the carotid artery.

FIG. 7(*a*) is a top view illustrating another exemplary relative position of a probe with respect to the carotid artery during IMT measurement, and FIG. 7(*b*) illustrates a tomographic image representing the carotid artery.

FIG. 8(*a*) is a top view illustrating still another exemplary relative position of a probe with respect to the carotid artery during IMT measurement, and FIG. 8(*b*) illustrates a tomographic image representing the carotid artery.

FIG. 14 is a block diagram illustrating a third embodiment of an ultrasonic diagnostic apparatus according to the present invention.

FIG. 15 is a block diagram illustrating a fourth embodiment of an ultrasonic diagnostic apparatus according to the present invention.

DESCRIPTION OF EMBODIMENTS

Hereinafter, embodiments of an ultrasonic diagnostic apparatus according to the present invention and a measuring method using the apparatus will be described in detail with reference to the accompanying drawings.

Embodiment 1

Figure 1:
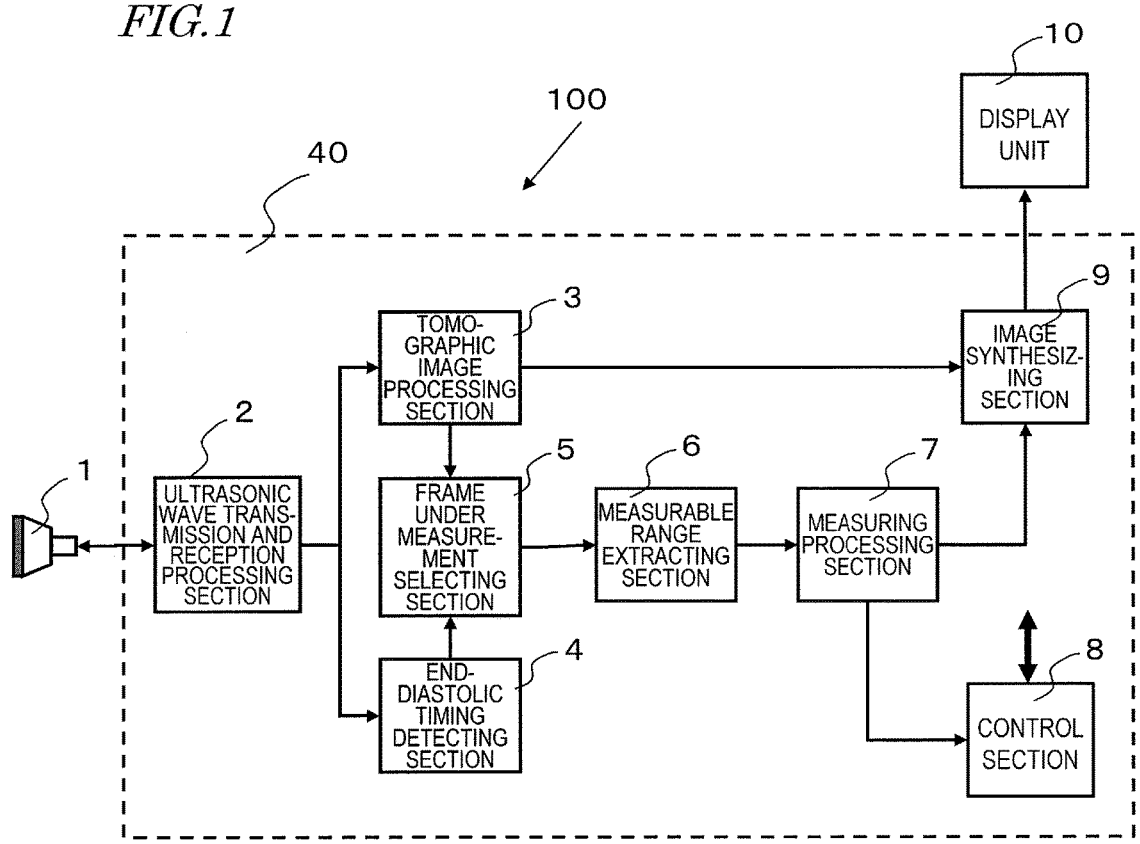
FIG. 1 is a block diagram illustrating a first embodiment of an ultrasonic diagnostic apparatus according to the present invention.

FIG. 1 is a block diagram illustrating a first embodiment of an ultrasonic diagnostic apparatus according to the present invention.

The ultrasonic diagnostic apparatus 100 shown in FIG. 1 includes a controller 40, which includes an ultrasonic wave transmission and reception processing section 2, a tomographic image processing section 3, an end of diastolic phase detecting section 4, a frame under measurement selecting section 5, a measurable range extracting section 6, a measuring processing section 7, a control section 8 and an image synthesizing section 9. In this embodiment, the ultrasonic diagnostic apparatus 100 does not include any probe 1 and a general-purpose probe 1 may be connected to the apparatus 100. However, the ultrasonic diagnostic apparatus 100 may include a probe 1.

The ultrasonic wave transmission and reception processing section 2, the frame under measurement selecting section 5, the control section 8 and the image synthesizing section 9 may be implemented as known hardware components using various electronic parts, for example. On the other hand, the tomographic image processing section 3, the end of diastolic phase detecting section 4, the measurable range extracting section 6 and the measuring processing section 7 may be implemented either by software or by hardware. If these sections are implemented by software, the received signal generated by the ultrasonic wave transmission and reception processing section 2 may be a digital signal. The control section 8 may be implemented as a combination of an arithmetic logic unit such as a microprocessor and software.

The probe 1 includes ultrasonic transducers, and transmits ultrasonic waves toward the subject, including a region of interest, and receives the ultrasonic waves reflected from the region of interest and converts those waves into an electrical signal, via those ultrasonic transducers. This first embodiment will be described on the supposition that what should be measured is the IMT. Thus, in this first embodiment, the region of interest refers herein to the IMT measuring range 30 shown in FIG. 16.

The ultrasonic wave transmission and reception processing section 2 is configured so that the probe 1 is readily attachable to, and removable from, itself. The ultrasonic wave transmission and reception processing section 2 performs transmission processing by driving the ultrasonic transducers of the probe 1 with drive pulses supplied to those transducers at predetermined timings so that the probe transmits ultrasonic waves. In addition, the ultrasonic wave transmission and reception processing section 2 receives, from the probe 1, an electrical signal to which the reflected ultrasonic wave received has been transformed, and subjects the electrical signal to various kinds of reception processing (including amplification and detection) that should be done to make ultrasonic tomographic images, thereby generating a received signal. The ultrasonic wave transmission and reception processing section 2 performs the transmission processing repeatedly and continuously to generate received signals sequentially, and generates multiple frames based on the received signals generated. In this description, a "frame" refers herein to either a set of received signals that need to be used to make a single tomographic image or a tomographic image that has been made based on a set of received signals.

Figure 16:
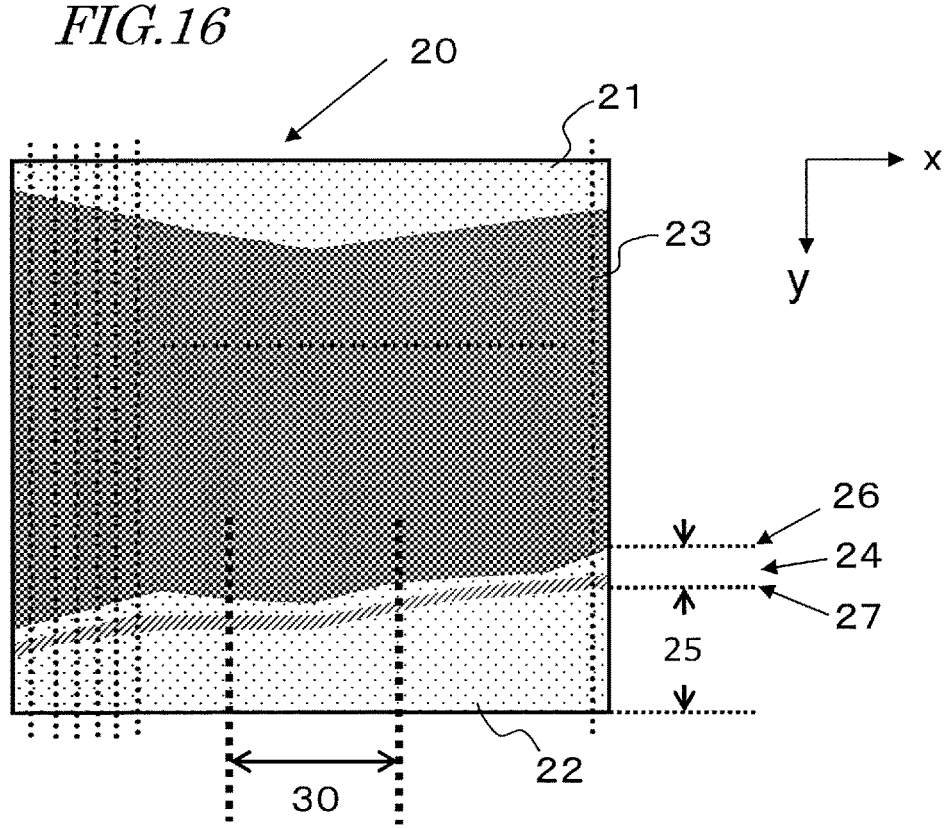
FIG. 16 illustrates a long-axis cross section of the carotid artery and an IMT measuring range.

The tomographic image processing section 3 receives the received signal that has been generated by the ultrasonic wave transmission and reception processing section 2, and performs coordinate transformation and other kinds of processing on the received signal, thereby making a tomographic image, which is a two-dimensional ultrasonic image, sequentially on a frame-by-frame basis. For example, the tomographic image processing section 3 makes tomographic images such as the one shown in FIG. 16 one after another. As shown in FIG. 16, by scanning the ultrasonic beam in the x direction, a received signal representing the reflected ultrasonic wave is obtained from each acoustic line (indicated by the dotted lines) that represent the path of the ultrasonic beam, thereby making a tomographic image for a single frame.

The end of diastolic phase detecting section 4 detects a timing indicating the end-diastolic timing based on the received signal that has been generated by the ultrasonic wave transmission and reception processing section 2. Specifically, first of all, the end of diastolic phase detecting section 4 processes the received signal that has been generated by the ultrasonic wave transmission and reception processing section 2 to obtain pulsation information of the blood vessel that is the object of measurement. In this description, the pulsation information of the blood vessel includes a variation in the inside diameter of the blood vessel. Also, the timing indicating the end-diastolic timing refers herein to the very last timing of a diastolic phase of the heart, i.e., a timing just before the heart starts to contract.

The frame under measurement selecting section 5 selects two or more frames under measurement to be subjected to the IMT measurement from multiple frames of the tomographic images that have been generated by the tomographic image processing section 3. In this first embodiment, multiple frames which cover a predetermined period that includes the end-diastolic timing detected by the end of diastolic phase detecting section 4 and that precedes and succeeds that end-diastolic timing are selected as the frames under measurement.

The measurable range extracting section 6 extracts ranges in which the measuring processing can be carried out easily from the region of interest included in each frame under measurement on a frame under measurement basis.

The measuring processing section 7 performs a predetermined kind of measuring processing on the measurable ranges that have been extracted by the measurable range extracting section 6. In measuring the IMT, first of all, the measuring processing section 7 detects two vascular boundaries, namely, the lumen-intima boundary 26 and the media-adventitia boundary 27, from the carotid artery 20 that is the region of interest in the IMT measuring range 30 and calculates the distance between the lumen-intima boundary 26 and media-adventitia boundary 27 detected as an IMT value, thereby performing measuring processing. In this case, the IMT value may be either max IMT that is the maximum value of the distance between the lumen-intima boundary 26 and the media-adventitia boundary 27 in the IMT measuring range 30 or mean IMT that is the average distance between those two boundaries. Alternatively, the IMT value may also be obtained by performing any other arithmetic operation or statistical processing.

The control section 8 controls the respective blocks and regards a result of measurement obtained by the measuring processing section 7 as a final IMT measured value. Optionally, to allow the operator to monitor such a tomographic image, on which the IMT measured value has been determined, on a display unit 10 (to be described later), the control section 8 may also control this apparatus so that when the IMT measured value is determined, the apparatus enters a freeze state automatically. In this case, in the field of ultrasonic diagnostic apparatuses, the "freeze state" generally refers to a state in which transmission and reception of ultrasonic waves is suspended AND the image displayed is frozen on the screen. In this embodiment, however, the "freeze state" may refer to not only such a state where the image on the screen is frozen with transmission and reception of ultrasonic waves suspended but also a state where either transmission and reception of ultrasonic waves is suspended OR the image on the screen is frozen as well.

The image synthesizing section 9 is configured so that the display unit 10 is connectable to itself, and synthesizes together the tomographic image generated by the tomographic image processing section 3 and the result of measurement obtained by the measuring processing section 7 so that the image and the result can be displayed together on the display unit 10 connected.

The display unit 10 is a monitor which is connected to the image synthesizing section 9 and which displays its image signal thereon.

Figure 2:
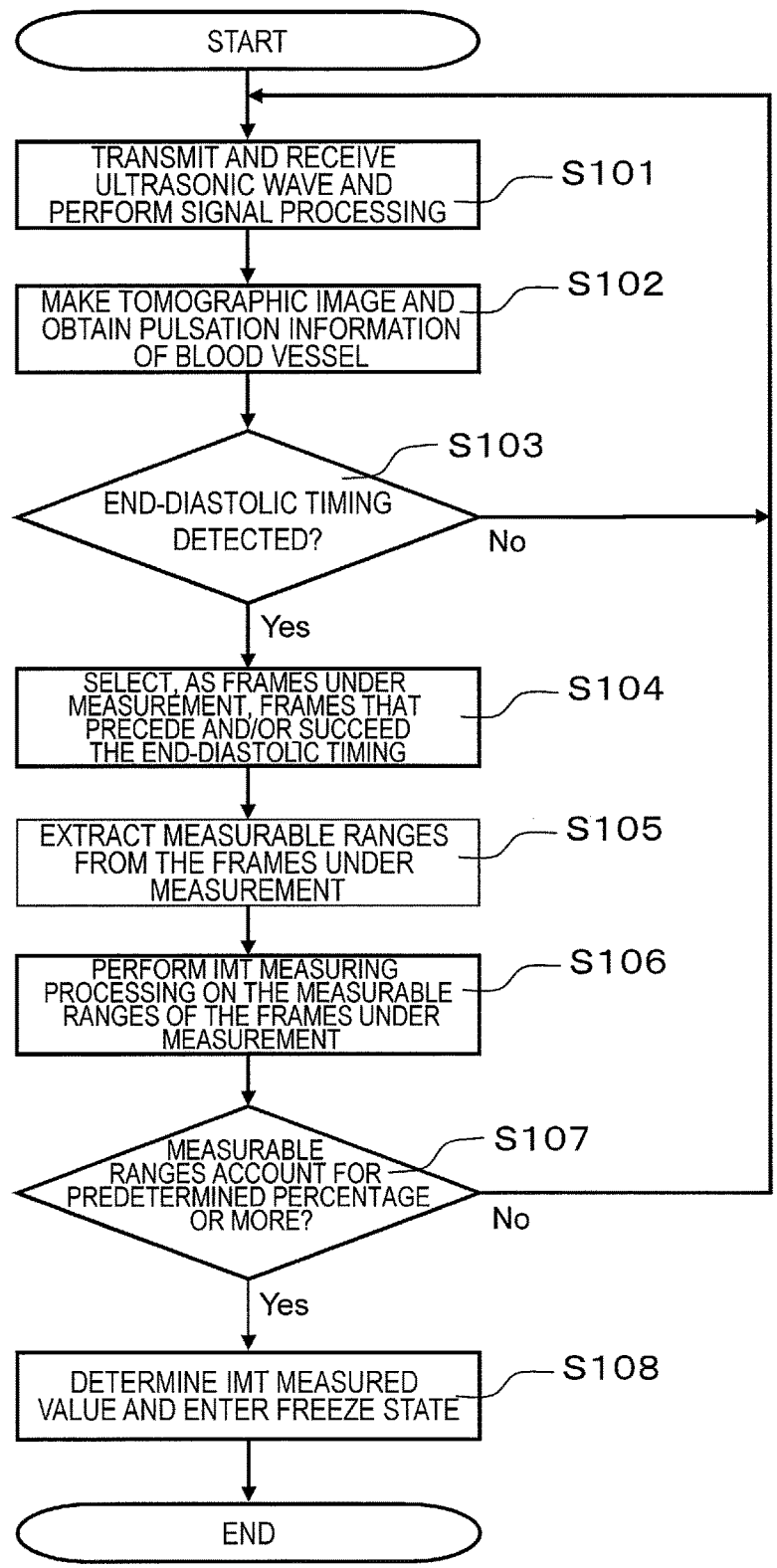
FIG. 2 is a flowchart showing how the ultrasonic diagnostic apparatus of the first embodiment of the present invention operates.

Hereinafter, it will be described how the ultrasonic diagnostic apparatus 100 of this first embodiment operates by taking a situation where the apparatus is used to measure the IMT value as an example. FIG. 2 is a flowchart showing typically how the ultrasonic diagnostic apparatus 100 of the first embodiment operates.

First, in Step S101, the ultrasonic wave transmission and reception processing section 2 performs ultrasonic signal transmission and reception controls. Specifically, the ultrasonic wave transmission and reception processing section 2 transmits ultrasonic waves by driving the probe 1. In addition, the ultrasonic wave transmission and reception processing section 2 subjects reflected ultrasonic waves which have been reflected from the subject's carotid artery and received at the probe 1 to signal processing just like an ordinary ultrasonic diagnostic apparatus, thereby generating a received signal. And the ultrasonic wave transmission and reception processing section 2 combines together a set of received signals thus generated to obtain a received signal for a single frame. Then, the received signal corresponding to a single frame is passed to the tomographic image processing section 3 and the end of diastolic phase detecting section 4. This processing is carried out a number of times at mutually different points in time. That is to say, one received signal for a single frame is obtained after another sequentially.

Next, in Step S102, the received signals supplied from the ultrasonic wave transmission and reception processing section 2 are processed by the tomographic image processing section 3, thereby making multiple tomographic images corresponding to a number of frames at multiple different times.

Subsequently, in Step S103, the end of diastolic phase detecting section 4 analyzes the received signal supplied from the ultrasonic wave transmission and reception processing section 2, obtains the pulsation information of the blood vessel, and detects the timing indicating the end-diastolic timing. If the timing detected does not indicate the end-diastolic timing, then the process goes back to the processing step S101 to continue the ultrasonic wave transmission and reception processing. On the other hand, if the timing detected indicates the end-diastolic timing, then the process advances to the next processing step S104.

It should be noted that the end-diastolic timing can be detected by the technique disclosed in Japanese Patent No. 4189405, for example. Hereinafter, that technique for detecting the end-diastolic timing will be described specifically with reference to FIG. 3(*a*) through 3(*b*).

FIG. 3(*a*) schematically illustrates a cross section of a blood vessel in the long-axis direction, and FIG. 3(*b*) illustrates a waveform showing a variation in the inside diameter of the blood vessel that is the distance between a measuring point A on the anterior wall 21 of the blood vessel and another measuring point B on its posterior wall 22. The blood vessel will contract according to the amount or rate of blood flowing inside itself. As the blood flow rate increases and the blood pressure rises in the systolic phase of the heart, the inside diameter of the blood vessel in that systolic phase (i.e., the distance between the two points A and B described above) increases and the vascular wall thickness decreases. On the other hand, as the blood flow rate decreases and the blood pressure falls in the diastolic phase of the heart, the inside diameter of the blood vessel in that diastolic phase decreases and the vascular wall thickness increases. That is to say, as the vascular wall thickness varies synchronously with the heartbeat, the IMT value also changes depending on the timing of measurement. Consequently, since the inner wall of the blood vessel varies with time as blood is pumped out of the heart, the pulsed waveform such as the one shown in FIG. 3(*b*) is observed.

Such a variation will be described more specifically by reference to the R-wave trigger timings of an ECG (indicated by the peaks of the lower waveform shown in FIG. 3(*b*)), which is usually used to detect the end-diastolic timing of the heart, as disclosed in Non-Patent Document No. 1. As shown in FIG. 3(*b*), the inner wall thickness of the blood vessel changes as blood is pumped out of the heart. The inside diameter of the blood vessel once decreases immediately after the R-wave trigger timing of the ECG but increases steeply after that and then gradually returns to the original value. The end-diastolic timing is a point in time when the inside diameter becomes the smallest just before starting to increase steeply. Even though the R-wave trigger timing of the ECG is regarded as indicating the end-diastolic timing of the heart, it takes some time for the heartbeat to reach the carotid artery. That is why there is a time lag between the respective ends of a diastolic phase at the carotid artery and at the heart. For that reason, according to this embodiment, the end-diastolic timing is defined herein to be the timing when the inside diameter of the blood vessel becomes the smallest just before starting to increase steeply as described above. It is recommended that the IMT value be measured when the vascular wall comes to have the maximum thickness. That is why the ideal timing to measure the IMT value is the end-diastolic timing.

In view of these considerations, by analyzing the amplitude and phase of the received signal with the measuring points A and B set on the anterior and posterior walls 21 and 22 of the blood vessel that is the object of measurement as shown in FIG. 3(*a*), the motion of these measuring points A and B is tracked. Since the artery repeatedly contracts and dilates as the heart beats, the distance between the measuring points A and B changes periodically as shown in FIG. 3(*b*). Thus, such a periodic variation is detected as a waveform representing a variation in the inside diameter of the blood vessel. And a timing when the inside diameter starts to increase steeply is detected by reference to the inside diameter variation waveform, and a timing earlier than the former timing by a certain amount of time is defined to be the end-diastolic timing.

In the first embodiment described above, the end-diastolic timing is supposed to be detected based on the received signal in order to detect the best timing to measure the IMT value easily. Optionally, however, the end-diastolic timing may also be detected using a normal ECG. In that case, there is no need to send a signal from the ultrasonic wave transmission and reception processing section 2 to the end of diastolic phase detecting section 4 in FIG. 1 and an ECG is connected to the end of diastolic phase detecting section 4.

If the end of diastolic phase detecting section 4 has detected a timing indicating the end-diastolic timing in Step S103, then the frame under measurement selecting section 5 selects, in Step S104, a plurality of frames which covers a predetermined period that includes the end-diastolic timing and that precedes and succeeds it as frames under measurement to be subjected to the IMT measurement by reference to the timing indicating the end-diastolic timing that has been detected by the end of diastolic phase detecting section 4.

Even though it is recommended in the foregoing description that the IMT value be measured when the thickness of the vascular wall becomes maximum, the IMT value hardly changes just before and right after the end-diastolic timing (particularly for a period preceding the end-diastolic timing which may last for, but does not have to be, approximately 100 ms) because the blood vessel contracts relatively gently in that period. That is why strictly speaking, frames falling within this period have not been obtained at the timing indicating the end-diastolic timing but can actually be used in practice to measure the IMT value. Optionally, instead of selecting frames under measurement from such a period that precedes and succeeds the end-diastolic timing, a predetermined number of frames that precede and succeed the end-diastolic timing may be selected as frames under measurement. Specifically, if the frame rate is 30 frames per second, for example, three frames that precede the end-diastolic timing may be selected. In this manner, frames that cover that 100 ms period preceding the end-diastolic timing can be selected. Consequently, essentially there is no significant difference between selecting a predetermined number of frames that precede the end-diastolic timing and setting a period that precedes and succeeds the end-diastolic timing to select frames to be obtained in that period.

Furthermore, to use frames that precede the end-diastolic timing detected as frames under measurement, a portion of the tomographic image corresponding to the required number of frames may be buffered in a memory, for example, and the buffered tomographic image may be selected as soon as the end-diastolic timing is detected. Such tomographic image buffering means is not shown in FIG. 1.

To measure the IMT value accurately, the vascular lumen-intima boundary 26 and media-adventitia boundary 27 should be rendered clearly on the received signal. For that purpose, in Step S105, the measurable range extracting section 6 extracts ranges that can be used for measurement from the region of interest rendered in each frame under measurement. To measure the vascular wall thickness accurately, the probe 1 should catch the vicinity of the center of a short-axis cross section of the blood vessel. Thus, the measurable range extracting section 6 extracts ranges that have been shot by making the ultrasonic beam pass through the vicinity of the center of the blood vessel from the region of interest rendered in each frame under measurement. Hereinafter, this operation will be described more specifically.

FIGS. 4(a) and 4(b) illustrate the relative positions of a probe put on the subject with respect to a short-axis cross section of the blood vessel.

Generally speaking, an ultrasonic wave is reflected from a boundary between two regions that have mutually different acoustic impedances (e.g., from a boundary between two tissues). In this case, the closer to 90 degrees the angle of incidence defined by the ultrasonic wave with respect to the boundary, the more strongly the ultrasonic wave will be reflected and the clearer the reflected echo signal will be. That is why if the probe 1 is put on the subject so as to catch the vicinity of the center of the blood vessel as shown in FIG. 4(a) (i.e., if the acoustic line of the ultrasonic wave as indicated by the dashed line passes through the vicinity of the center of the blood vessel), the ultrasonic wave will be incident perpendicularly onto the lumen-intima boundary 26 and the media-adventitia boundary 27 and strong and clear reflected echo signals are obtained from both of the two boundaries 26 and 27. On the other hand, unless the acoustic line of the ultrasonic wave passes through the vicinity of the center of the blood vessel as shown in FIG. 4(b), the ultrasonic wave will not be incident perpendicularly onto the two boundaries of the blood vessel and only weak and unclear reflected echo signals are obtained. As a result, the lumen-intima and media-adventitia boundaries 26 and 27 may be rendered as blurred and indistinct ones or the lumen-intima boundary may be rendered.

Consequently, in the region of interest in each frame under measurement, a clear echo signal can be obtained from a range that has been shot with the ultrasonic beam passing through the vicinity of the center of the blood vessel, but only an unclear echo signal is obtained from a range that has been shot with the ultrasonic beam not passing through the vicinity of the center of the blood vessel. That is why such a range from which only an unclear echo signal has been obtained is not used for measurement and a range from which a clear echo signal has been obtained is extracted as a range that can be used for measurement. This processing is carried out on each frame under measurement.

More specifically, the measurable range extracting section 6 provisionally detects the two kinds of vascular boundaries, namely, the vascular lumen-intima boundary 26 and media-adventitia boundary 27, by reference to the luminance information of the tomographic image. Next, the measurable range extracting section 6 sees if on the tomographic image, there is any portion in which the luminance rises from one side of the detected lumen-intima boundary 26 closer to the vascular lumen 23 toward the intima-media complex 24 on the acoustic line that passes the boundary 26, if there is any portion in which the luminance rises from one side of the detected media-adventitia boundary 27 closer to the intima-media complex 24 toward the adventitia on the acoustic line that passes that boundary 27, and if there is any portion in which the luminance falls on the acoustic lines between the lumen-intima and media-adventitia boundaries 26 and 27 detected as shown in FIG. 16. In this manner, the measurable range extracting section 6 determines whether or not the lumen-intima and media-adventitia boundaries 26 and 27 are rendered clearly at the vascular boundary locations on the tomographic image. Based on the result of this decision, the measurable range extracting section 6 determines and extracts the measurable ranges.

In this case, the vicinity of the center of a short-axis cross section of the blood vessel where the two boundaries can be rendered clearly may be defined by the distance between the acoustic line shown in FIG. 4(a) and the center of the cross section of the blood vessel, which may be 0.5 mm or less. But the distance will vary according to the subject, the precision of measurement of the ultrasonic diagnostic apparatus and the condition of measurement, and should not always be exactly equal to that value.

Hereinafter, it will be described more specifically how this apparatus works in measuring an IMT value, for example.

Figure 5:
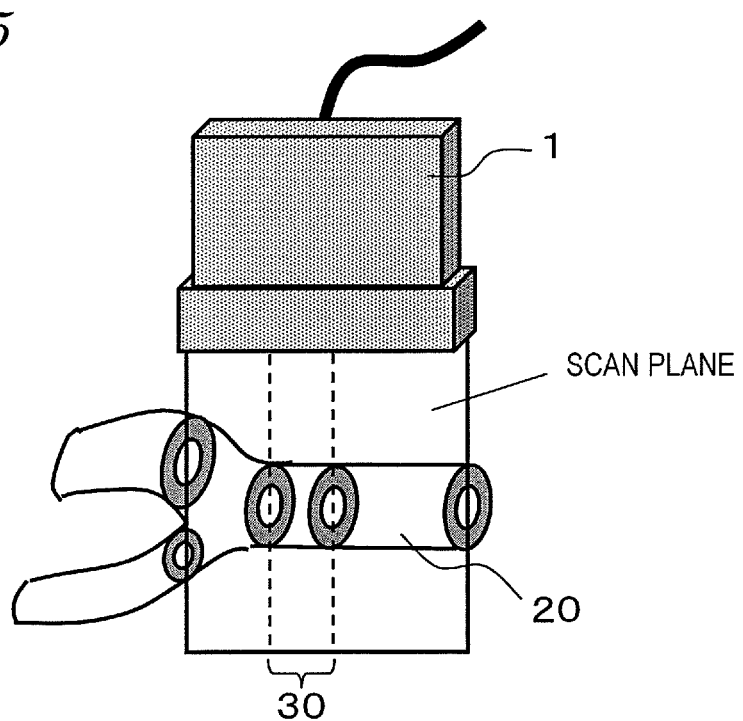
FIG. 5 is a perspective view illustrating the relative position of the probe with respect to the carotid artery during IMT measurement.

In measuring an IMT value, generally the measurement is made on the basis of a predetermined length. For example, 1 cm is the recommended length of the IMT measuring range 30. That is why the probe 1 is arranged to be aligned with a long-axis cross section of the carotid artery 20 (i.e., a cross section that crosses the short-axis direction of the blood vessel at right angles) so that the probe 1 can catch the vicinity of the center of the blood vessel in the IMT measuring range 30 with a length of 1 cm as shown in FIG. 5. More specifically, the probe 1 is arranged with respect to the subject so that the longitudinal direction of the probe surface becomes parallel to the long-axis direction of the carotid artery 20 and that a scan plane formed by scanning ultrasonic beams includes the center axis of the carotid artery 20.

If the probe 1 is arranged in the long-axis direction of the carotid artery 20 so as to catch the vicinity of the center 31 of a short-axis cross section of the carotid artery 20 as shown in FIG. 6(a), then the probe 1 catches the vicinity of the center 31 of the carotid artery 20 in the entire IMT measuring range 30. This can be said to be an ideal state. In that case, on the tomographic image, the lumen-intima boundary 26 and the media-adventitia boundary 27 are rendered clearly in the entire IMT measuring range 30 as shown in FIG. 6(b). Consequently, since the IMT can be measured in the entire IMT measuring range 30, the entire IMT measuring range 30 is extracted as a measurable range.

However, as the IMT measuring range 30 is too long for the range in the vicinity of the center 31 of the carotid artery 20, it is difficult for everybody but a well-experienced skilled person to put the probe 1 at the right position shown in FIG. 6(a). That is why if an ordinary operator puts the probe 1, then the probe 1 will be put improperly as shown in FIG. 7(a) or 8(a).

FIG. 7(a) illustrates a situation where the probe 1 is put obliquely with respect to the long-axis direction of the carotid artery 20 and catches the vicinity of the center 31 of the blood vessel only at a middle portion of the IMT measuring range 30. In that case, the lumen-intima boundary 26 and the media-adventitia boundary 27 are clearly rendered only at the middle portion of the IMT measuring range 30 but are rendered unclearly at the end portions. That is to say, as shown in FIG. 7(*b*), the boundaries are rendered clearly only in the range where the probe 1 has caught the vicinity of the center 31 of the blood vessel (i.e., at the portions of the lumen-intima boundary 26 and media-adventitia boundary 27 as indicated by the solid lines) but are rendered unclearly everywhere else (i.e., at the rest of the lumen-intima boundary 26 and media-adventitia boundary 27 as indicated by the dashed lines). Consequently, the end portions of the IMT measuring range as indicated by the dashed lines are regarded as ranges where the lumen-intima boundary 26 and media-adventitia boundary 27 are rendered too unclearly to measure the IMT, and only its middle portion as indicated by the solid lines is extracted as a measurable range.

As in FIG. 7(*a*), FIG. 8(*a*) also illustrates a situation where the probe 1 that should be arranged parallel to the long-axis direction of the carotid artery 20 is put obliquely with respect to the long-axis direction of the carotid artery 20 and catches the vicinity of the center 31 of the carotid artery 20 only at a right end portion of the IMT measuring range 30. In that case, as shown in FIG. 8(*b*), neither the lumen-intima boundary 26 nor the media-adventitia boundary 27 is rendered at the left end portion, which means that the probe 1 is too located distant from the vicinity of the center 31 of the blood vessel there to render those boundaries on the tomographic image. Consequently, the right end portion of the IMT measuring range (as indicated by the solid lines) and the middle portion of the IMT measuring range 30 are extracted as measurable ranges but the other portion cannot be used for measuring the IMT.

After the measurable ranges have been extracted from each frame under measurement, the process advances to Step S106, in which the measuring processing section 7 performs IMT measuring processing.

First of all, the measuring processing section 7 detects the two kinds of vascular boundaries, namely, the vascular lumen-intima boundary 26 and media-adventitia boundary 27, in the IMT measuring range 30 of each frame under measurement by reference to the luminance information of the tomographic image and other pieces of information. In this case, the processing of detecting these boundaries is performed on a range of the tomographic image where the lumen-intima boundary 26 and media-adventitia boundary 27 are rendered clearly, i.e., on the measurable range. Alternatively, part of the result of the provisionary detection obtained by the measurable range extracting section 6, i.e., a result of measurement indicating the measurable range, may be output to the measuring processing section 7 so that the measuring processing section 7 can measure the IMT based on that result provided. The IMT value is calculated based on the distance between the lumen-intima boundary 26 and media-adventitia boundary 27 that have been detected.

After having calculated the IMT value in each frame under measurement, the measuring processing section 7 combines together the measurable ranges of respective frames under measurement, thereby determining a final IMT value. This procedure will be described in further detail below.

Figure 9:
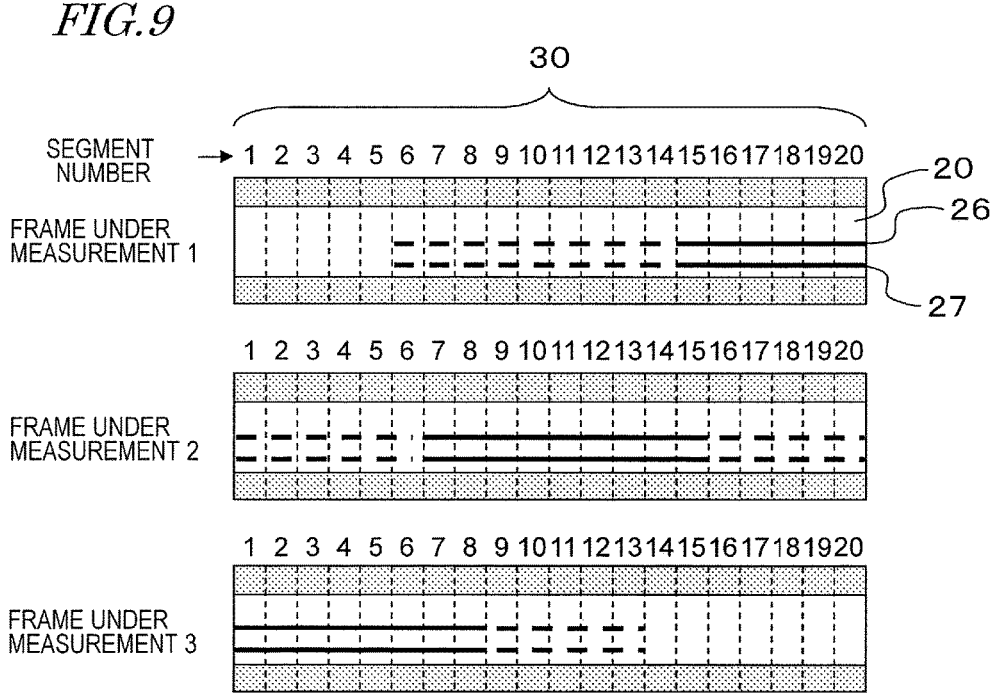
FIG. 9 shows how the lumen-intima boundary and media-adventitia boundary are rendered on the tomographic images in a situation where there are three frames in a predetermined period that precedes and succeeds the end-diastolic timing.

FIG. 9 shows the results of detection of the lumen-intima boundary 26 and media-adventitia boundary 27 on the tomographic image in three frames under measurement that have been obtained in a predetermined period that precedes and succeeds the end-diastolic timing. The "segment number" shown in FIG. 9 is defined to be either the location or the order of a segment that is a reference unit (length) on which the measurable range extracting section 6 determines whether or not a given range is a measurable range. For example, if the IMT measuring range 30 has a length of 1 cm and divided into twenty segments, then each segment has a length of 0.5 mm. The segment length may be determined according to the resolution of the probe 1 used or the IMT measuring precision required.

In FIG. 9, each segment in which the lumen-intima boundary 26 and media-adventitia boundary 27 are drawn in solid lines is a segment in which these boundaries are rendered clearly and is a range that has been extracted as a measurable range by the measurable range extracting section 6. On the other hand, each segment in which the lumen-intima boundary 26 and media-adventitia boundary 27 are drawn in dashed lines is a segment in which these boundaries are rendered unclearly, and each segment in which no boundaries are drawn is a segment in which none of these boundaries have been detected. These segments are ranges that have not been extracted as measurable ranges by the measurable range extracting section 6. As shown in FIG. 9, even if multiple frames are obtained for different periods of time by putting the probe 1 at a predetermined position, some segments are measurable ranges but other segments are not, because the internal body tissue including the carotid artery is moving and because the probe 1 that the operator thinks is "fixed" is actually shaking slightly.

As shown in FIG. 9, in Segments #1 through #6 of Frame under Measurement #3, the lumen-intima boundary 26 and the media-adventitia boundary 27 are rendered clearly. That is why in the range of these segments, the IMT value is measured on the tomographic image of Frame under Measurement #3.

As for Segments #7 and #8, the lumen-intima boundary 26 and media-adventitia boundary 27 are rendered clearly in both of Frames under Measurement #2 and #3. That is why in these segments, the IMT value is measured on the tomographic images of Frames under Measurement #2 and #3. To combine the two frames together, the lumen-intima boundary and media-adventitia boundary may be detected and the IMT value may be calculated in each of those frames and the average of the IMT values may be obtained on a segment-by-segment basis. Alternatively, a frame in which the lumen-intima boundary 26 and media-adventitia boundary 27 are rendered more clearly may be selected on a segment-by-segment basis and may be used to detect the lumen-intima boundary 26 and media-adventitia boundary 27 and calculate the IMT value.

Processing is carried out in the same way on the other segments. Specifically, as for Segments #9 through #14, the IMT value is calculated based on the tomographic image of Frame under Measurement #2. As for Segment #15, the IMT value is calculated based on the tomographic images of Frames under Measurement #1 and #2. And as for Segments #16 through #20, the IMT value is calculated based on the tomographic image of Frame under Measurement #1.

By measuring the IMT values with the three frames under measurement #1 to #3 combined in this manner, even though only a part of the IMT measuring range 30 is a measurable range in each of these frames under measurement #1 to #3, the IMT value can be measured in substantially the entire IMT measuring range 30. If the IMT value is measured on a segment-by-segment basis and if the maximum value of the IMT values of all segments is determined, max IMT can be obtained. On the other hand, if the average of the IMT values of all segments is calculated, then mean IMT can be obtained.

In the example illustrated in FIG. 9, the measuring processing section 7 measures the IMT values in the entire IMT measuring range 30 by combining the measurable ranges that have been extracted by the measurable range extracting section 6 from respective frames under measurement. However, even if the measurable ranges extracted from the respective frames under measurement are combined together, the IMT values sometimes cannot be measured in the entire IMT measuring range 30. In that case, the IMT values may be measured locally by using only the measurable ranges extracted from the IMT measuring range 30. In such a situation, the broader the measurable range (i.e., the larger the number of measurable segments), the more accurately max IMT or mean IMT can be measured.

If the probe 1 has shifted and failed to catch the vicinity of the vascular center 31 of the carotid artery 20 as shown in FIGS. 7 and 8, then the IMT values should be unable to be measured in a sufficient part of the IMT measuring range 30. That is why in order to cancel the shift, the position of the probe 1 needs to be adjusted. However, if the object of measurement is as thin as the carotid artery 20, the probe 1 should be moved very finely in order to adjust the position of the probe 1 and have the probe 1 catch the vicinity of the center 31 of the blood vessel as shown in FIG. 6 and this is a very difficult job to do for everybody but a skilled person. Also, even if the probe 1 has once been put successfully at the right position as shown in FIG. 6, it is also difficult to keep the probe 1 held at such a position.

However, according to the present invention, even if the probe 1 cannot be held at the right position and even if the range (segment) in which the probe 1 is catching the vicinity of the center 31 of the blood vessel has changed, the IMT values can still be measured appropriately as long as the measurable range accounts for a significant percentage of the IMT measuring range 30 by combining multiple frames under measurement together. Consequently, even an unskilled person can also measure the IMT values easily.

In this case, if the IMT value can be measured in a predetermined percentage or more of the IMT measuring range 30, then a control operation may be performed so as to regard the IMT value as a final IMT measured value and end the measurement on the supposition that max IMT and mean IMT to be obtained based on these IMT values is a sufficiently accurate one. Hereinafter, this control operation will be described in detail with reference to FIG. 2.

After the IMT value has been measured in each segment of the IMT measuring range 30 in Step S106 as described above, the control section 8 determines, in the next processing step S107, whether or not the total of the measurable ranges in the frames under measurement that have been used in the IMT measuring processing by the measuring processing section 7 accounts for a predetermined percentage of the entire IMT measuring range 30. In this case, unless the total accounts for the predetermined percentage, the process goes back to the processing step S101 to continue the measurement. On the other hand, if the total of the measurable ranges accounts for the predetermined percentage or more, the process advances to Step S108, in which the control section 8 determines an IMT measured value. Optionally, by making the apparatus enter the freeze state automatically in that case, the operator can monitor, on the display unit 10, the tomographic image, of which the IMT measured values has been finally determined.

The percentage to be accounted for by the total of the measurable ranges in order to determine the IMT measured value may be set to be either 100% (i.e., the entire IMT measuring range 30 with a length of 1 cm, for example) or a predetermined ratio that is less than one. If this ratio is increased, the accuracy of the IMT value increases. On the other hand, if this ratio is decreased, the IMT value can be measured even when the probe shifts from the right position to a certain degree. As a result, the operator can use this apparatus more easily. For example, if the ratio is set to be 75% of the IMT measuring range 30 and if the total length of the measurable ranges is equal to or greater than 7.5 mm, the IMT measured value can be determined. In the example in which the IMT measuring range 30 with a width of 1 cm is divided into twenty segments, each having a width of 0.5 mm, as described above, the IMT measured value can be determined if there are fifteen or more measurable segments.

To further increase the accuracy, the control operation may also be performed so as to determine the IMT measured value and end the measurement if the measurable ranges located at the same position overlap with each other in at least a predetermined number of measurable frames and if the ratio of such overlapping measurable ranges accounts for a predetermined percentage or more of the IMT measuring range 30.

A specific example will be described with reference to FIG. 10, in which the segments, solid lines and dashed lines mean the same as in FIG. 9. In this example, if the IMT values can be measured in two or more frames under measurement in 75% or more (i.e., fifteen or more segments) of the IMT measuring range 30, the IMT measured value is supposed to be determined and the measurement is supposed to be ended.

Figure 10:
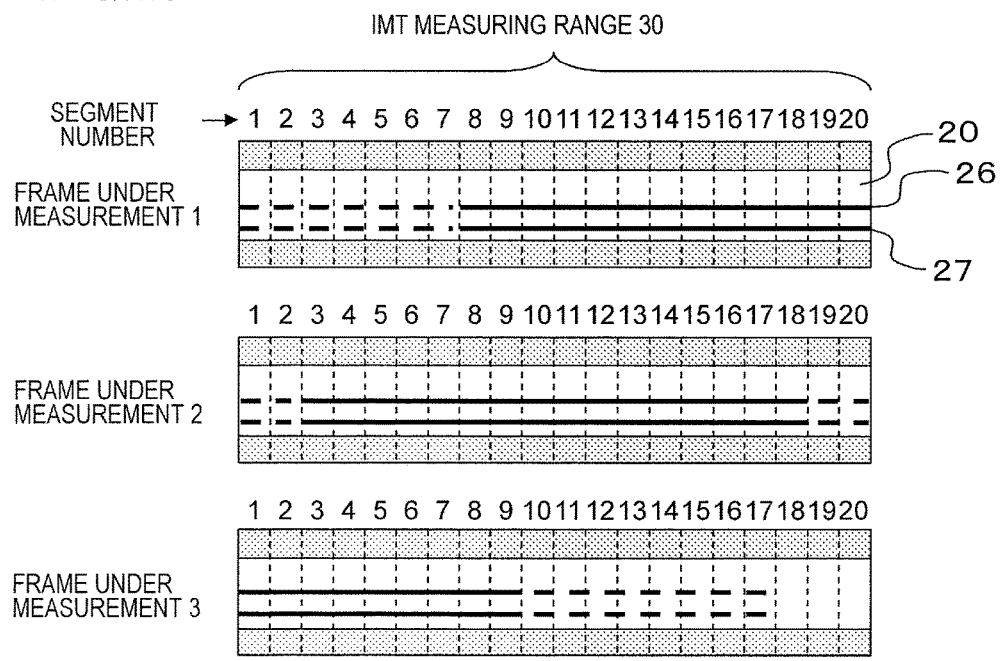
FIG. 10 shows how the lumen-intima boundary and media-adventitia boundary are rendered on the tomographic images in a situation where there are three frames in a predetermined period that precedes and succeeds the end-diastolic timing.

As shown in FIG. 10, as for Segments #1 and #2, the IMT value can be measured only in one frame under measurement #3; as for Segments #3 through #7, the IMT values can be measured in two frames under measurement #2 and #3; as for Segments #8 and #9, the IMT values can be measured in all of the three frames under measurement #1 to #3; as for Segments #10 through #18, the IMT values can be measured in two frames under measurement #1 and #2; and as for Segments #19 and #20, the IMT value can be measured only in one frame under measurement #1. As a result, the IMT values can be measured in two or more frames under measurement in sixteen segments #3 through #18, which accounts for 75% (corresponding to fifteen segments) or more of the IMT measuring range 30. That is why the control section 8 determines the IMT measured value and ends the measurement.

On the other hand, if the same condition (if the IMT values can be measured in two or more frames under measurement in 75% or more of the IMT measuring range 30, then the IMT measured value is determined and the measurement is ended) were applied to the example shown in FIG. 9, then the IMT values could be measured in two or more frames under measurement only in three segments #7, #8 and #15. That is why if the results shown in FIG. 9 are obtained, then the IMT value measuring process is not ended but continued by going back to the processing step S101.

By measuring the IMT values in such a procedure, a more accurate measured value can be obtained compared to a situation where the IMT measured value is determined if the IMT values can be measured in one of multiple frames under measurement. Although not shown in FIG. 2, if the image synthesizing section 9 synthesizes together the IMT measured value obtained by the measuring processing section 7 and the tomographic image made by the tomographic image processing section 3 and outputs the synthetic image to the display unit 10, the operator can check out the diagnostic image and the result of measurement on the screen at the same time.

In the embodiment described above, the present invention has been described as being applied to measuring the IMT value of the carotid artery. However, this is just an example of the present invention and this invention is naturally applicable to any other measurement. For instance, the present invention is also applicable to measuring the IMT of the femoral artery. Alternatively, this embodiment can also be used with an image that renders clearly the anterior and posterior walls of the blood vessel defined to be a measurable range when the vascular diameter of the abdominal artery is measured. Furthermore, even when an embryo is measured, this embodiment can also be used with an image that renders clearly a region of interest such as a thigh bone defined as a measurable range.

Embodiment 2

Figure 11:
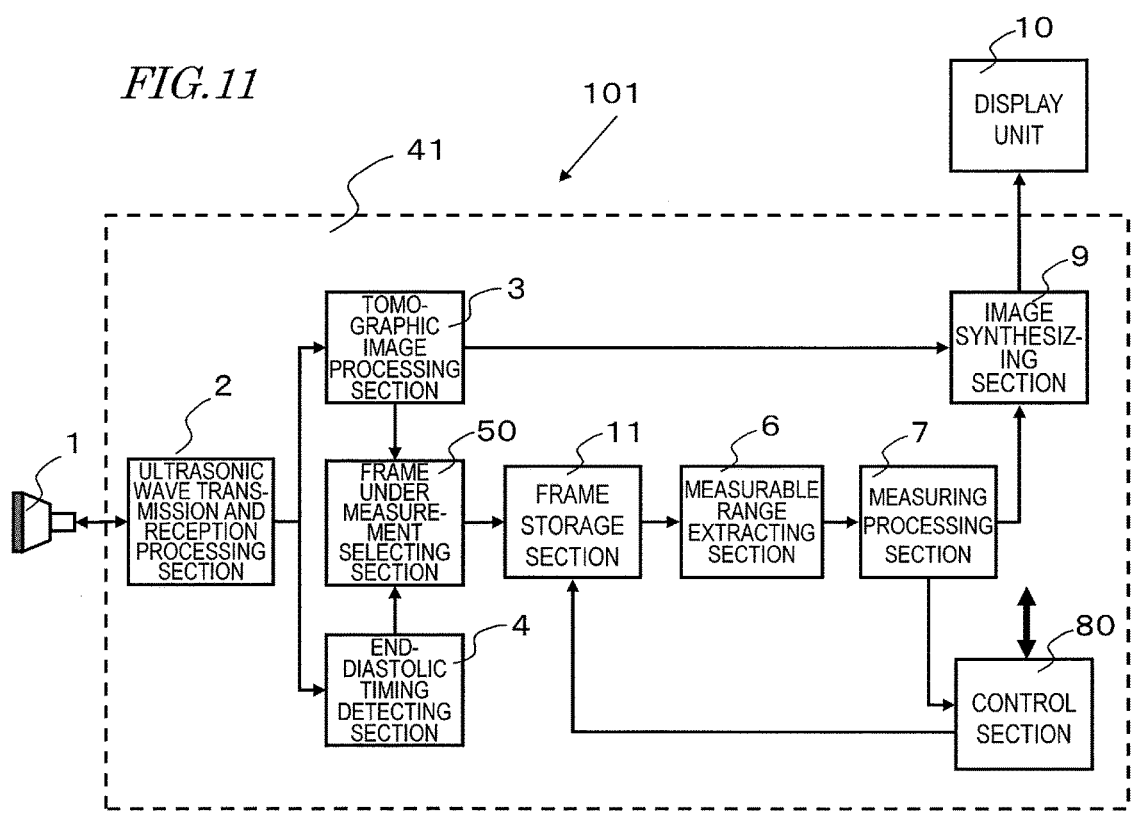
FIG. 11 is a block diagram illustrating a second embodiment of an ultrasonic diagnostic apparatus according to the present invention.

FIG. 11 is a block diagram illustrating a second embodiment of an ultrasonic diagnostic apparatus according to the present invention. In FIG. 11, any block having substantially the same function as its counterpart of the first embodiment is identified by the same reference numeral and its description will be omitted herein. This second embodiment will also be described as being applied to measuring the IMT value of the carotid artery.

This ultrasonic diagnostic apparatus 101 includes a controller 41, which includes the ultrasonic wave transmission and reception processing section 2, the tomographic image processing section 3, the end of diastolic phase detecting section 4, a frame under measurement selecting section 50, a frame storage section 11, the measurable range extracting section 6, the measuring processing section 7, a control section 80 and the image synthesizing section 9.

Just like the frame under measurement selecting section 5 of the first embodiment, the frame under measurement selecting section 50 also selects multiple frames under measurement to be subjected to the IMT measurement from multiple frames of the tomographic images that have been generated by the tomographic image processing section 3. The frame under measurement selecting section 5 of the first embodiment selects, as the frames under measurement, multiple frames which cover a predetermined period that precedes and succeeds that end-diastolic timing that has been detected by the end of diastolic phase detecting section 4. On the other hand, the frame under measurement selecting section 50 of this embodiment selects, as the frames under measurement, multiple frames to be obtained at timings indicating respective ends of diastolic phases that have been detected by the end of diastolic phase detecting section 4 during one cardiac cycle.

The frame storage section 11 not only stores those frames at respective ends of diastolic phases that have been selected by the frame under measurement selecting section 50 but also retrieves multiple tomographic images stored and passes them as frames under measurement to the measurable range extracting section 6.

Just like the control section 8 of the first embodiment, the control section 80 also controls the respective blocks and regards a result of measurement obtained by the measuring processing section 7 as a final IMT measured value. Optionally, to allow the operator to monitor such a tomographic image, on which the IMT measured value has been determined, on the display unit 10, the control section 80 may also control this apparatus so that when the IMT measured value is determined, the apparatus enters a freeze state automatically. However, unlike the control section 8 of the first embodiment, this control section 80 performs a control operation of discarding the frames (tomographic images) that have been stored in the frame storage section 11 if a predetermined condition is satisfied.

Figure 12:
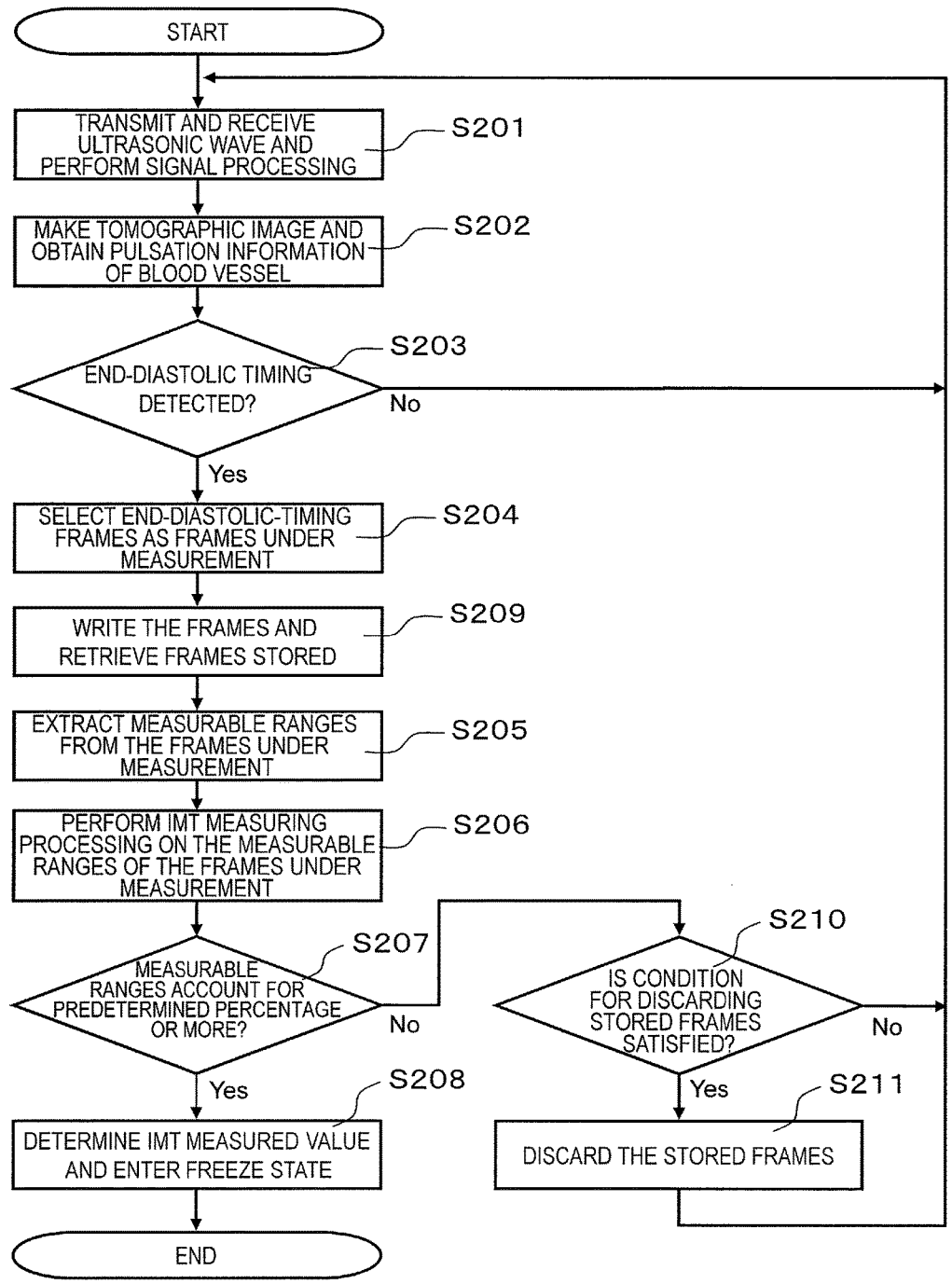
FIG. 12 is a flowchart showing how the ultrasonic diagnostic apparatus of the second embodiment of the present invention operates.

Hereinafter, it will be described how the ultrasonic diagnostic apparatus 101 of this second embodiment works in measuring the IMT value, for example. FIG. 12 is a flowchart showing typically how the ultrasonic diagnostic apparatus of this second embodiment operates.

The probe 1, ultrasonic wave transmission and reception processing section 2, tomographic image processing section 3 and end of diastolic phase detecting section 4 operate in the same way as their counterparts of the first embodiment. And Steps S201, S202 and S203 shown in FIG. 12 respectively correspond to Steps S101, S102 and S103 shown in FIG. 2.

As in the processing step S103, if it has turned out, in Step S203, that the timing detected by the end of diastolic phase detecting section 4 is not the end-diastolic timing, the process goes back to Step S201 to continue the ultrasonic wave transmission and reception processing. On the other hand, if the timing detected by the end of diastolic phase detecting section 4 has turned out to be the end-diastolic timing, then the process advances to the next processing step S204.

In Step S204, the frame under measurement selecting section 50 selects, as a frame under measurement to be used for measuring the IMT value, a frame of the tomographic image corresponding to the timing of the end-diastolic timing of each cardiac cycle that has been detected by the end of diastolic phase detecting section 4.

Next, in Step S209, the frame storage section 11 writes the frame of the tomographic image at the end-diastolic timing that has been selected by the frame under measurement selecting section 50. And then the frame storage section 11 retrieves a number of end-of-diastolic-phase frames of the tomographic image that have been stored for a predetermined cardiac rate (e.g., three frames if the predetermined cardiac rate is three) and outputs them as frames under measurement to the measurable range extracting section 6.

In this processing step, if the number of frames stored by the frame storage section 11 is less than the predetermined number of frames (e.g., three), then only stored frames may be used as frames under measurement. Or although not shown in FIG. 12, the process may go back to the processing step S201 to continue the ultrasonic wave transmission and reception processing.

The measurable range extracting section 6 and the measuring processing section 7 operate in the same way as their counterparts of the first embodiment. And the processing steps S205 and S206 respectively correspond to the processing steps S105 and S106 of the first embodiment. In this embodiment, however, the frames under measurement are frames at respective ends of diastolic phases for multiple cardiac cycles that have been retrieved from the frame storage section 11.

Just as the control section 8 of the first embodiment does in Step S107, the control section 80 determines, in Step S207, whether or not the total of the measurable ranges in the frames under measurement that have been used in the IMT measuring processing by the measuring processing section 7 accounts for a predetermined percentage or more of the entire IMT measuring range 30. In this case, if this condition is satisfied, the control section 80 determines an IMT measured value in Step S208 just as the control section 8 of the first embodiment does in Step S108. In this case, the control section 80 may also control the apparatus so that the apparatus enters the freeze state automatically as in the first embodiment described above.

Unless the predetermined condition is satisfied in Step S207, the control section 80 determines, in Step S210, whether or not the frames (tomographic images) stored in the frame storage section 11 should be discarded. This decision can be made in the following situations, for example.

Firstly, if there are no measurable ranges at all in the frame under measurement associated with the latest heartbeat, then the frames stored in the frame storage section 11 may be discarded. If there are no measurable ranges at all, then it means that the probe 1 has completely lost track of the vicinity of the center 31 of the blood vessel and it can be said that the measurement has discontinued. That is why in such a situation, the previous frames are discarded so as not to be used for measurement from now on.

Secondly, if a predetermined operation has been performed by the operator and if that operating event has been accepted by the control section 80, then the frames stored in the frame storage section 11 may be discarded. Such an operating section and a path leading from the operating section to the control section 80 are not shown in FIG. 11. Examples of predetermined operations include: changing the measuring ranges; changing parameters (including a scan line density, whether parallel reception is performed or not, the number of lines used for the parallel reception, a transmission frequency, a transmission power, and a transmission interval) about the ultrasonic wave transmission and reception processing performed by the ultrasonic wave transmission and reception processing section 2; and changing parameters (including a gain, a dynamic range, whether filter processing needs to be performed or not, or a property of the filter processing) about the generation of a tomographic image by the tomographic image processing section 3. If these parameters have been changed, then it means that the measuring condition has changed from the previous one, and therefore, the previous frames are discarded so as not to be used for measurement from now on.

Thirdly, if the apparatus has sensed that the probe 1 has been moved significantly by the operator, the frames stored in the frame storage section 11 may be discarded. Such a probe movement sensing section and a path leading from the sensing section to the control section 80 are not shown in FIG. 11. The movement of the probe 1 may be sensed by detecting a variation in the tomographic image or by providing an angle sensor or any other kind of sensor for the probe 1, for example. If the probe 1 has moved significantly, then it means that the region of interest is now different from what used to be, and therefore, the previous frames are discarded so as not to be used for measurement from now on.

If any of these conditions is satisfied, then the frames stored in the frame storage section 11 are discarded in Step S211. And no matter whether that condition is satisfied in Step S210 or not, the process goes back to the processing step S201 to continue measurement.

Figure 13:
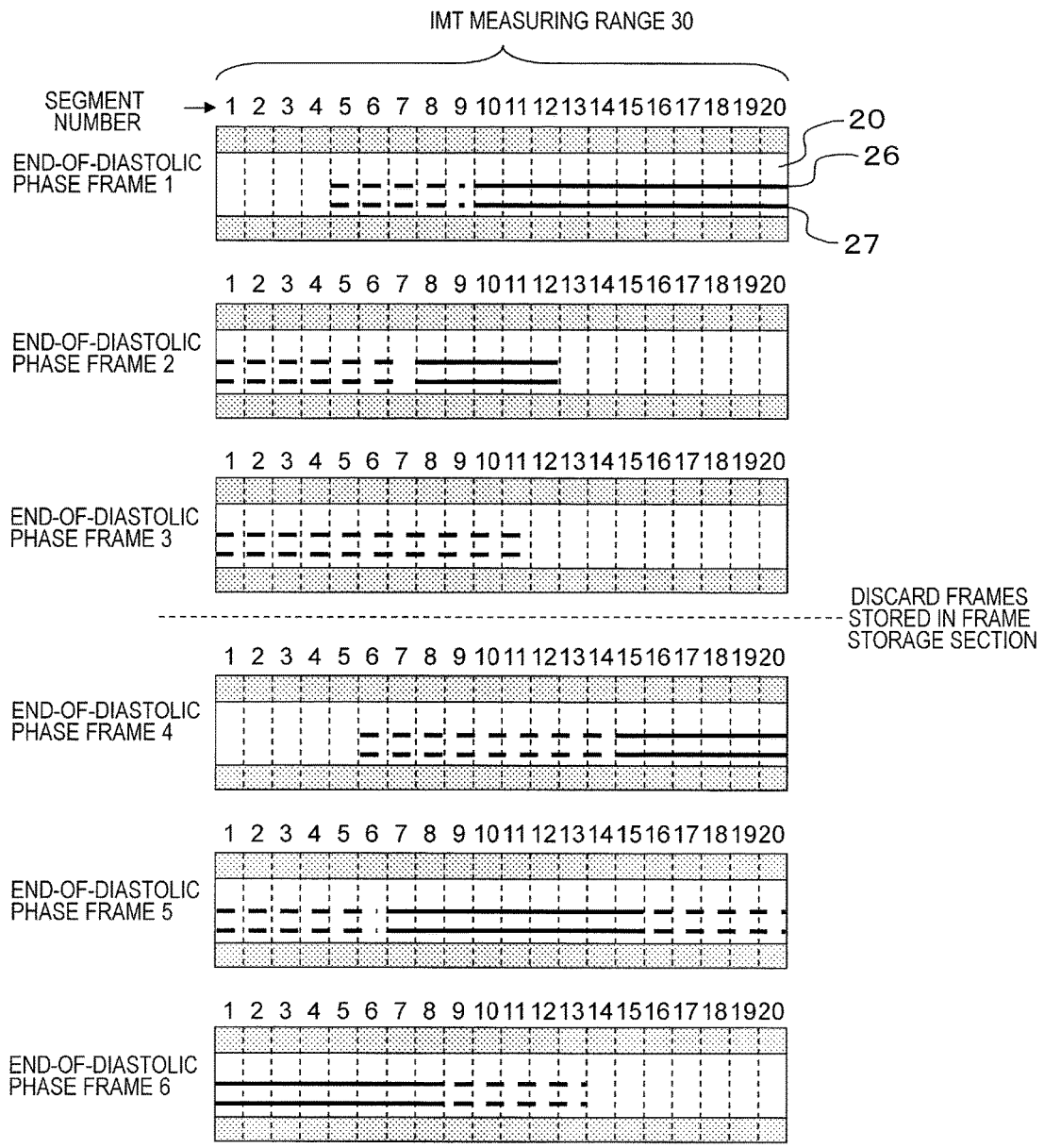
FIG. 13 shows how the lumen-intima boundary and media-adventitia boundary are rendered on the tomographic images corresponding to frames at respective ends of diastolic phases in six cardiac cycles.

This procedure will be described more specifically with reference to FIG. 13, which illustrates how the lumen-intima boundary and media-adventitia boundary are rendered on respective tomographic images of six End-of-Diastolic-Phase Frames #1 through #6 that have been selected as frames under measurement for six heartbeats. In this example, frames preceding End-of-Diastolic-Phase Frame #1 are not taken into account for the sake of simplicity. The meanings of the segments, solid lines and dashed lines shown in FIG. 13 are the same as those of the first embodiment shown in FIG. 9. In Step S207, if in any of the frames under measurement, the IMT values can be measured in the entire IMT measuring range 20 (i.e., in all of twenty segments), the IMT measured value is supposed to be determined and the measurement is supposed to be ended.

First of all, at the end-diastolic timing for the first heartbeat, the frame under measurement selecting section 50 selects End-of-Diastolic-Phase Frame #1 and the data of that frame is written on the frame storage section 11. Then, End-of-Diastolic-Phase Frame #1 is retrieved from the frame storage section 11 and output to the measurable range extracting section 6. In response, the measurable range extracting section 6 extracts Segments #10 through #20 as a measurable range and the measuring processing section 7 measures the IMT using the segments of the measurable range extracted. Next, the control section 80 determines whether or not the measurable range accounts for a predetermined ratio. With only this End-of-Diastolic-Phase Frame #1, the IMT value can be measured in just eleven segments, and therefore, the IMT measured value cannot be determined yet.

Next, at the end-diastolic timing for the second heartbeat, the frame under measurement selecting section 50 selects End-of-Diastolic-Phase Frame #2 and the data of that frame is written on the frame storage section 11. Then, End-of-Diastolic-Phase Frames #1 and #2 are retrieved from the frame storage section 11 and output to the measurable range extracting section 6. As in the first heartbeat, the measurable range extracting section 6 and the measuring processing section 7 perform the operations described above, and the control section 80 determines whether or not the measurable range accounts for a predetermined ratio. Even with these End-of-Diastolic-Phase Frames #1 and #2 combined, the IMT value can be measured in just thirteen segments #8 through #20, and therefore, the IMT measured value cannot be determined yet.

Next, at the end-diastolic timing for the third heartbeat, the frame under measurement selecting section 50 selects End-of-Diastolic-Phase Frame #3 and the data of that frame is written on the frame storage section 11. Then, End-of-Diastolic-Phase Frames #1 to #3 are retrieved from the frame storage section 11. In response, the measurable range extracting section 6 and the measuring processing section 7 perform the operations described above. As shown in FIG. 13, there are no measurable segments at all in End-of-Diastolic-Phase Frame #3. That is why the control section 80 concludes that a condition for discarding the frames stored in the frame storage section 11 is satisfied, and instructs the frame storage section 11 to discard the data of those End-of-Diastolic-Phase Frames #1 to #3. As a result, even with these End-of-Diastolic-Phase Frames #1 to #3 combined, the IMT measured value cannot be determined yet and the measurement needs to be made all over again (in Steps S210, S211 and S201).

Next, at the end-diastolic timing for the fourth heartbeat, the frame under measurement selecting section 50 selects End-of-Diastolic-Phase Frame #4 and the data of that frame is written on the frame storage section 11. Since the previous frames have already been discarded by the frame storage section 11, only End-of-Diastolic-Phase Frame #4 is retrieved from the frame storage section 11. After that, the same processing is carried out and the control section 80 determines whether or not the measurable range accounts for a predetermined ratio. With this End-of-Diastolic-Phase Frame #4, the IMT value can be measured in just six segments #15 through #20, and therefore, the control section 80 does not determine the IMT measured value yet.

Next, at the end-diastolic timing for the fifth heartbeat, the frame under measurement selecting section 50 selects End-of-Diastolic-Phase Frame #5 and the data of that frame is written on the frame storage section 11. Then, End-of-Diastolic-Phase Frames #4 and #5 are retrieved from the frame storage section 11. Even with these End-of-Diastolic-Phase Frames #1 and #2 combined, the IMT value can be measured in just fourteen segments #7 through #20, and therefore, the control section 80 does not determine the IMT measured value yet.

Next, at the end-diastolic timing for the sixth heartbeat, the frame under measurement selecting section 50 selects End-of-Diastolic-Phase Frame #6 and the data of that frame is written on the frame storage section 11. Then, End-of-Diastolic-Phase Frames #4 to #6 are retrieved from the frame storage section 11. In response, the measurable range extracting section 6 and the measuring processing section 7 perform the operations described above, thus measuring the IMT value. By combining these End-of-Diastolic-Phase Frames #4 to #6 together, the IMT value can now be measured in all of the segments #1 through #20. Thus, the control section 80 concludes that the measurable range accounts for a predetermined ratio or more and regards the IMT value measured by the measuring processing section 7 as a final IMT measured value. In this manner, the measurement gets done. In this case, the apparatus may also be controlled so as to enter the freeze state automatically as in the first embodiment.

As described above, according to this embodiment, even if the measurable range of an end-of-diastolic-phase frame associated with one heartbeat does not account for a sufficient percentage of the IMT measuring range 30 but if the total of multiple measurable ranges accounts for a sufficiently large percentage of the IMT measuring range 30 by combining multiple end-of-diastolic-phase frames together for multiple heartbeats, the IMT value can still be measured appropriately. As a result, the IMT value can be measured easily.

Optionally, just like the frame under measurement selecting section 5 of the first embodiment, the frame under measurement selecting section 50 of this embodiment may also select, as frames under measurement, multiple frames (e.g., three frames) that precede and succeed the end-diastolic timing. In that case, the frame storage section 11 writes those three selected frames at a time. The measurable range extracting section 6, measuring processing section 7 and control section 8 perform the processing described above by using three frames under measurement for one heartbeat.

Also, in that case, if there are no measurable ranges at all in any of the three frames under measurement for one heartbeat, then the control section 80 may conclude that the frames stored in the frame storage section 11 be discarded. Likewise, if there are no measurable ranges at all in at least one or two of the three frames under measurement for one heartbeat, then the control section 80 may conclude that the frames stored in the frame storage section 11 be discarded.

As in the first embodiment described above, the ultrasonic diagnostic apparatus of this embodiment can also be used to measure various values other than the IMT value of the carotid artery.

Embodiment 3

FIG. 14 is a block diagram illustrating a third embodiment of an ultrasonic diagnostic apparatus according to the present invention. In FIG. 14, any block having substantially the same function as its counterpart of the first embodiment is identified by the same reference numeral and its description will be omitted herein. This third embodiment will also be described as being applied to measuring an IMT value.

In the first embodiment described above, the IMT value is supposed to be measured on a tomographic image. In this embodiment, however, the IMT value is measured based on the received signal, which is a major difference from the first embodiment. Although the IMT value is measured according to this embodiment based on the received signal itself, the IMT value may also be measured based on information to make a tomographic image (e.g., luminance information) that needs to be generated based on the received signal.

This ultrasonic diagnostic apparatus 102 includes a controller 42, which includes the ultrasonic wave transmission and reception processing section 2, the tomographic image processing section 3, the end of diastolic phase detecting section 4, a frame under measurement selecting section 51, a measurable range extracting section 61, a measuring processing section 71, a control section 81 and the image synthesizing section 9.

The ultrasonic wave transmission and reception processing section 2 outputs a received signal generated to not only the tomographic image processing section 3 and the end of diastolic phase detecting section 4 but also the frame under measurement selecting section 51 as well.

The frame under measurement selecting section 51 selects two or more frames under measurement to be subjected to the IMT measurement from multiple frames represented by the received signals that have been generated by the ultrasonic wave transmission and reception processing section 2. In this first embodiment, multiple frames which cover a predetermined period that includes the end-diastolic timing detected by the end of diastolic phase detecting section 4 and that precedes and succeeds that end-diastolic timing are selected as the frames under measurement as in the first embodiment described above.

Just like the measurable range extracting section 6 the first embodiment, the measurable range extracting section 61 extracts ranges in which the measuring processing can be carried out easily from the region of interest included in each frame under measurement on a frame under measurement basis. In this embodiment, however, the data of the frame to process is not the luminance information of the tomographic image but the received signal itself. That is why the measurable range to be extracted is not an area on the tomographic image but a part of a group of received signals forming the frame which can be subjected to the measuring processing.

Just like the measuring processing section 7 of the first embodiment, the measuring processing section 71 performs a predetermined kind of measuring processing on the measurable ranges that have been extracted by the measurable range extracting section 61. In this embodiment, however, the data of each frame to be subjected to the measuring processing is not the luminance information of the tomographic image but the received signal itself.

The measurable range extracting section 61 and measuring processing section 71 perform the processing described above by reference to the amplitude information of the received signals that form each frame instead of the luminance information of the tomographic image. As a result, the measurable range extracting section 61 and measuring processing section 71 can perform the same processing as the measurable range extracting section 6 and the measuring processing section 7 of the first embodiment. Specifically, instead of determining whether or not the lumen-intima boundary 26 and media-adventitia boundary 27 are rendered clearly on the tomographic image in performing the processing of extracting the measurable range, the decision is made whether or not there is any sensible variation in the amplitude corresponding to the lumen-intima boundary 26 and media-adventitia boundary 27 on the received signal. Also, in performing the processing of measuring the IMT value, two kinds of vascular boundaries, namely, the vascular lumen-intima boundary 26 and media-adventitia boundary 27, are detected from the measurable range, i.e., part of the group of received signals forming the frame which can be subjected to the measuring processing, by reference to the amplitude information of the received signal.

Just like the control section 8 of the first embodiment, the control section 81 controls the respective blocks and regards the result of measurement obtained by the measuring processing section 71 as a final IMT measured value. Optionally, to allow the operator to monitor such a tomographic image, on which the IMT measured value has been determined, on the display unit 10, the control section 81 may also control this apparatus so that when the IMT measured value is determined, the apparatus enters a freeze state automatically.

The ultrasonic diagnostic apparatus 102 of this third embodiment operates just as already described for the first embodiment with reference to the flowchart shown in FIG. 2 except that the amplitude information of received signals that form a frame is used instead of the luminance information of the tomographic image.

According to this embodiment, the measurable range is extracted and the measuring processing is carried out by reference to the amplitude information of the received signals, not the tomographic image. That is why unlike the first embodiment, the processing can be carried out without depending on the settings or parameters when the tomographic image is made.

As in the first embodiment described above, the ultrasonic diagnostic apparatus of this embodiment can also be used to measure various values other than the IMT value of the carotid artery.

Embodiment 4

FIG. 15 is a block diagram illustrating a fourth embodiment of an ultrasonic diagnostic apparatus according to the present invention. In FIG. 15, any block having substantially the same function as its counterpart of the first to third embodiments is identified by the same reference numeral and its description will be omitted herein. This fourth embodiment will also be described as being applied to measuring the IMT value of the carotid artery.

In the second embodiment described above, the IMT value is supposed to be measured on a tomographic image. In this embodiment, however, the IMT value is measured based on the received signal, which is a major difference from the first embodiment. Although the IMT value is measured according to this embodiment based on the received signal itself, the IMT value may also be measured based on information to make a tomographic image (e.g., luminance information) that needs to be generated based on the received signal, as in the third embodiment described above.

This ultrasonic diagnostic apparatus 103 includes a controller 43, which includes the ultrasonic wave transmission and reception processing section 2, the tomographic image processing section 3, the end of diastolic phase detecting section 4, a frame under measurement selecting section 52, the measurable range extracting section 61, the measuring processing section 71, a control section 82 and the image synthesizing section 9.

The ultrasonic wave transmission and reception processing section 2 outputs a received signal generated to not only the tomographic image processing section 3 and the end of diastolic phase detecting section 4 but also the frame under measurement selecting section 52 as well.

The frame under measurement selecting section 52 selects two or more frames under measurement to be subjected to the IMT measurement from multiple frames represented by the received signals that have been generated by the ultrasonic wave transmission and reception processing section 2. In this first embodiment, multiple frames at the timings indicating respective ends of diastolic phases that have been detected by the end of diastolic phase detecting section 4 are selected as frames under measurement as in the second embodiment described above.

The frame storage section 12 not only stores the received signals forming those frames at respective ends of diastolic phases that have been selected by the frame under measurement selecting section 50 but also retrieves the received signals representing multiple frames stored and passes them as frames under measurement to the measurable range extracting section 61. The frame storage section 12 operates in the same way as the frame storage section 11 of the second embodiment described above except that this frame storage section 12 writes received signals that form the frames instead of the luminance information of the tomographic image.

The measurable range extracting section 61 and measuring processing section 71 operate just as already described for the third embodiment.

Just like the control section 80 of the second embodiment, the control section 82 also controls the respective blocks and regards a result of measurement obtained by the measuring processing section 71 as a final IMT measured value. Also, if a predetermined condition is satisfied, the control section 82 performs the processing of discarding the frames (received signals) that are stored on the frame storage section 12. Optionally, to allow the operator to monitor such a tomographic image, on which the IMT measured value has been determined, on the display unit 10, the control section 82 may also control this apparatus so that when the IMT measured value is determined, the apparatus enters a freeze state automatically.

The ultrasonic diagnostic apparatus 103 of this fourth embodiment operates just as already described for the second embodiment with reference to the flowchart shown in FIG. 12 except that the amplitude information of received signals that form a frame is used instead of the luminance information of the tomographic image.

According to this embodiment, the measurable range is extracted and the measuring processing is carried out by reference to the amplitude information of the received signals, not the tomographic image. That is why unlike the second embodiment, the processing can be carried out without depending on the settings or parameters when the tomographic image is made.

As in the first embodiment described above, the ultrasonic diagnostic apparatus of this embodiment can also be used to measure various values other than the IMT value of the carotid artery.

As can be seen, the ultrasonic diagnostic apparatus according to any of the first through fourth embodiments described above allows even a non-skilled person to measure the IMT value, the vascular diameter, an embryo, or any other internal body tissue of the subject both easily and accurately.

In addition, according to the first through fourth embodiments described above, based on either received signals forming multiple frames that have been obtained at multiple different times or the tomographic image, respective measurable ranges are extracted and then combined together, thereby performing measuring processing. That is why the measurement described above can also get done even without using a sophisticated probe such as a 3D probe or a 4D probe. That is to say, the measurement can also get done accurately even by using an array probe, which is a simple probe used generally and in which transducers are arranged one-dimensionally.

INDUSTRIAL APPLICABILITY

Even if a probe has shifted from the right position on the subject and cannot track the region of interest just as intended, the ultrasonic diagnostic apparatus according to the present disclosure does not have to make precise adjustment of the probe's position in order to cancel the shift. But only if the measurable range accounts for a significant percentage of the region of interest by combining multiple frames under measurement together, the ultrasonic diagnostic apparatus can also perform the measuring processing appropriately.

As a result, even if the probe fails to be put at such a right position, the state of the region of interest can also be measured properly. Consequently, even a non-skilled person can also make the measurement easily and accurately.

Therefore, this is an apparatus which is so easy to use as to accept users with a wide variety of skills, and this apparatus can be used effectively and extensively to measure the IMT value of the carotid artery or to make measurement on any of various internal body tissues or any particular region thereof.

REFERENCE SIGNS LIST 1 probe
2 ultrasonic wave transmission and reception processing section
3 tomographic image processing section
4 end of diastolic phase detecting section
5, 50, 51, 52 frame under measurement selecting section
6, 61 measurable range extracting section
7, 71 measuring processing section
8, 80, 81, 82 control section
9 image synthesizing section
10 display unit
11, 12 frame storage section
20 carotid artery
21 anterior wall
22 posterior wall
23 vascular lumen
24 intima-media
25 adventitia
26 lumen-intima boundary
27 media-adventitia boundary
30 IMT measuring range
31 approximate center of blood vessel
40, 41, 42, 43 controller
100, 101, 102, 103 ultrasonic diagnostic apparatus

The invention claimed is:

1. An ultrasonic diagnostic apparatus which is configured so that a probe including transducers is connectable to the apparatus and which performs measurement of a parameter on a subject's region of interest, the apparatus comprising:
a controller configured to perform transmission processing, in which an ultrasonic wave is transmitted toward the subject including the region of interest by driving the probe, and received signal processing, in which frames are generated based on the probe's received signals representing the ultrasonic wave that has been reflected from the subject including the region of interest, a number of times at mutually different points in time, thereby generating multiple frames, and
to select at least two frames under measurement to be subjected to measurement from the multiple frames, and
to extract measurable ranges for each of the at least two frames, on which the measurement of the parameter is able to be carried out, based on respective received signals obtained from the region of interest that is represented in the at least two frames under measurement, wherein each of the measurable ranges of the at least two frames covers a different portion of the region of interest, and
to combine the measurable ranges together to produce a combined measurable range and to perform the measurement of the parameter on the combined measurable range of the region of interest.

2. The ultrasonic diagnostic apparatus of claim 1, wherein the controller makes multiple tomographic images, corresponding to the respective frames, based on the received signals that form the multiple frames, and
selects, based on portions of the region of interest on the tomographic images of the multiple frames, at least two frames under measurement to be subjected to measurement from the multiple frames, and
extracts the measurable ranges, on which the measuring processing is able to be carried out, from those portions representing the region of interest on the tomographic images of the frames under measurement, and
combines the tomographic image portions on the measurable ranges together to perform the measurement of the parameter.

3. The ultrasonic diagnostic apparatus of claim 1, wherein if the combined measurable range accounts for a predetermined percentage or more of the entire region of interest, the controller regards a result of the measurement as a measured value.

4. The ultrasonic diagnostic apparatus of claim 1, wherein if the measurable ranges located at the same position overlap with each other in at least a predetermined number of the frames under measurement and if a combination of such overlapping measurable ranges accounts for a predetermined percentage or more of the entire region of interest, the controller regards a result of the measurement as a measured value.

5. The ultrasonic diagnostic apparatus of claim 1, wherein after having regarded the result of the measurement as a measured value, the controller controls the ultrasonic diagnostic apparatus to enter a freeze state automatically.

6. The ultrasonic diagnostic apparatus of claim 1, wherein the region of interest is a part of a blood vessel, and
wherein the controller extracts, as the measurable ranges, a region in which a lumen-intima boundary and a media-adventitia boundary are rendered, and measures, as the parameter, the intima-media thickness of the blood vessel using the combined measurable range along the blood vessel.

7. The ultrasonic diagnostic apparatus of claim 6, wherein the controller further detects the end-diastolic timing of the subject's cardiac cycle, and
selects, as the frames under measurement, multiple frames that have been obtained at different points in time within a predetermined period including the end-diastolic timing detected.

8. The ultrasonic diagnostic apparatus of claim 6, wherein the controller further detects the end-diastolic timing of the subject's cardiac cycle, and
selects, as the frames under measurement, a predetermined number of frames that precede and/or succeed the end-diastolic tinning detected.

9. The ultrasonic diagnostic apparatus of claim 6, wherein the controller further detects the end-diastolic timing of the subject's cardiac cycle,
selects and stores, as the frames under measurement, at least two of the frames that have been obtained at mutually different points in times indicating respective end-diastolic timings, and
extracts the measurable ranges from the at least two frames under measurement that have been stored.

10. The ultrasonic diagnostic apparatus of claim 9, wherein if any of the at least two frames under measurement that have been stored satisfies a predetermined condition, the controller discards the at least two frames under measurement that have been stored.

11. An ultrasonic measuring method for carrying out a predetermined kind of measurement of a parameter on a subject's region of interest using an ultrasonic wave generated by a probe, the method comprising the steps of:
(i) generating multiple frames by performing transmission processing, in which the ultrasonic wave is transmitted by driving the probe, and received signal processing, in which the frames are generated based on the probe's received signals representing the ultrasonic wave that has been reflected from the subject including the region of interest, a number of times at mutually different points in time;
(ii) selecting at least two frames under measurement to be subjected to measurement from multiple frames;
(iii) extracting measurable ranges for each of the at least two frames, on which the measurement of the parameter is able to be carried out, based on respective received signals obtained from the region of interest that is represented in the at least two frames under measurement, wherein each of the measurable ranges of the at least two frames covers a different portion of the region of interest; and
(iv) combining the measurable ranges together to produce a combined measurable range and to perform the measurement of the parameter on the combined measurable range of the the region of interest.

12. The ultrasonic measuring method of claim 11, wherein the step (i) includes making multiple tomographic images, corresponding to the respective frames, based on the received signals that form the multiple frames, and
wherein the step (ii) includes selecting, based on portions of the region of interest on the tomographic images of the multiple frames, at least two frames under measurement to be subjected to measurement from the multiple frames, and
wherein the step (iii) includes extracting the measurable ranges, on which the measuring processing is able to be carried out, from those portions representing the region of interest on the tomographic images of the frames under measurement, and
wherein the step (iv) includes combining those measurable ranges of the tomographic image portions together to perform the measurement of the parameter on the tomographic images representing the region of interest.

13. The ultrasonic diagnostic apparatus of claim 6, wherein each of the measurable ranges cover the different portion of a length of the blood vessel.

14. The ultrasonic diagnostic apparatus of claim 13, wherein the measurable ranges are combined on a segment by segment basis of the region of interest.

15. The ultrasonic diagnostic apparatus of claim 14, wherein any overlapping segments of the measurable ranges are averaged.

* * * * *